United States Patent
Rhee et al.

(10) Patent No.: US 11,633,818 B2
(45) Date of Patent: Apr. 25, 2023

(54) DEVICES, SYSTEMS, AND METHODS FOR TREATMENT OF INTRACRANIAL ANEURYSMS

(71) Applicant: Covidien LP, Mansfield, MA (US)

(72) Inventors: Richard Rhee, Anaheim, CA (US); Vincent Divino, Mission Viejo, CA (US); Ashok Nageswaran, Irvine, CA (US); Junwei Li, Irvine, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/949,568

(22) Filed: Nov. 3, 2020

(65) Prior Publication Data
US 2021/0128162 A1 May 6, 2021
US 2022/0304696 A2 Sep. 29, 2022

Related U.S. Application Data

(60) Provisional application No. 62/930,303, filed on Nov. 4, 2019, provisional application No. 62/930,487, filed
(Continued)

(51) Int. Cl.
*B23P 19/04* (2006.01)
*A61B 17/12* (2006.01)
(Continued)

(52) U.S. Cl.
CPC ........ *B23P 19/047* (2013.01); *A61B 17/1214* (2013.01); *A61B 17/12031* (2013.01);
(Continued)

(58) Field of Classification Search
CPC . B23P 19/047; A61B 17/12; A61B 17/12031; A61B 17/12113;
(Continued)

(56) References Cited

U.S. PATENT DOCUMENTS 5,041,090 A 8/1991 Scheglov et al.
5,250,071 A 10/1993 Palermo
(Continued)

FOREIGN PATENT DOCUMENTS

CA 3031482 A1 8/2017
CN 101460102 A 6/2009
(Continued)

OTHER PUBLICATIONS

Barnett et al., Assessment of EmboGel—A Selectively Dissolvable Radiopaque Hydrogel for Embolic Applications, Journal of Vascular and Interventional Radiology: JVIR, Feb. 2011, 10 pages.
(Continued)

*Primary Examiner* — George J Ulsh
(74) *Attorney, Agent, or Firm* — Fortem IP LLP; Mary Fox

(57) ABSTRACT

Systems and methods for treating an aneurysm in accordance with embodiments of the present technology include intravascularly delivering an occlusive member to an aneurysm cavity via an elongated shaft and transforming a shape of the occlusive member within the cavity. The method may include introduction of an embolic element to a space between the occlusive member and an inner surface of the aneurysm wall. In some embodiments, the elongated shaft is detachably coupled to a distal portion of the occlusive member.

18 Claims, 17 Drawing Sheets

Related U.S. Application Data on Nov. 4, 2019, provisional application No. 62/930,324, filed on Nov. 4, 2019, provisional application No. 62/930,357, filed on Nov. 4, 2019, provisional application No. 62/930,333, filed on Nov. 4, 2019, provisional application No. 62/930,421, filed on Nov. 4, 2019.

(51) Int. Cl.
 *A61B 17/00* (2006.01)
 *A61B 90/00* (2016.01)

(52) U.S. Cl.
 CPC .. *A61B 17/12113* (2013.01); *A61B 17/12145* (2013.01); *A61B 17/12172* (2013.01); *A61B 17/12186* (2013.01); *A61B 17/12168* (2013.01); *A61B 2017/00526* (2013.01); *A61B 2017/00557* (2013.01); *A61B 2017/00862* (2013.01); *A61B 2017/00929* (2013.01); *A61B 2017/12054* (2013.01); *A61B 2017/12063* (2013.01); *A61B 2090/376* (2016.02); *A61B 2090/3966* (2016.02)

(58) Field of Classification Search
 CPC .......... A61B 17/1214; A61B 17/12145; A61B 17/12172; A61B 17/12186; A61B 2017/00526; A61B 2017/00557; A61B 2017/00862; A61B 2017/00929; A61B 2017/12054; A61B 2017/12063; A61B 2017/1209; A61B 2090/376; A61B 2090/3966; A61B 17/12181
 See application file for complete search history.

(56) References Cited

U.S. PATENT DOCUMENTS

| | | |
|---|---|---|
| 5,261,916 A | 11/1993 | Engelson |
| 5,284,488 A | 2/1994 | Sideris |
| 5,326,350 A | 7/1994 | Li |
| 5,354,295 A | 10/1994 | Guglielmi et al. |
| 5,405,379 A | 4/1995 | Lane |
| 5,417,708 A | 5/1995 | Hall et al. |
| 5,601,600 A | 2/1997 | Ton |
| 5,645,558 A | 7/1997 | Horton |
| 5,669,931 A | 9/1997 | Kupiecki et al. |
| 5,725,552 A | 3/1998 | Kotula et al. |
| 5,733,294 A | 3/1998 | Forber et al. |
| 5,741,333 A | 4/1998 | Frid |
| 5,749,891 A | 5/1998 | Ken et al. |
| 5,749,895 A | 5/1998 | Sawyer et al. |
| 5,749,919 A | 5/1998 | Blanc |
| 5,814,062 A | 9/1998 | Sepetka et al. |
| 5,823,198 A | 10/1998 | Jones et al. |
| 5,911,731 A | 6/1999 | Pham et al. |
| 5,916,235 A | 6/1999 | Guglielmi |
| 5,925,060 A | 7/1999 | Forber |
| 5,928,260 A | 7/1999 | Chin et al. |
| 5,935,148 A | 8/1999 | Villar et al. |
| 5,941,249 A | 8/1999 | Maynard |
| 5,944,738 A | 8/1999 | Amplatz et al. |
| 5,951,599 A | 9/1999 | Mccrory |
| 5,964,797 A | 10/1999 | Ho |
| 5,976,169 A | 11/1999 | Imran |
| 5,980,554 A | 11/1999 | Lenker et al. |
| 6,022,374 A | 2/2000 | Imran |
| 6,033,423 A | 3/2000 | Ken et al. |
| 6,036,720 A | 3/2000 | Abrams et al. |
| 6,063,070 A | 5/2000 | Eder |
| 6,063,104 A | 5/2000 | Villar et al. |
| 6,086,577 A | 7/2000 | Ken et al. |
| 6,090,125 A | 7/2000 | Horton |
| 6,093,199 A | 7/2000 | Brown et al. |
| 6,096,021 A | 8/2000 | Helm et al. |
| 6,123,715 A | 9/2000 | Amplatz |
| 6,139,564 A | 10/2000 | Teoh |
| 6,152,144 A | 11/2000 | Lesh et al. |
| 6,159,531 A | 12/2000 | Dang et al. |
| 6,165,193 A | 12/2000 | Greene, Jr. et al. |
| 6,168,615 B1 | 1/2001 | Ken et al. |
| 6,168,622 B1 | 1/2001 | Mazzocchi |
| 6,238,403 B1 | 5/2001 | Greene, Jr. et al. |
| 6,299,619 B1 | 10/2001 | Greene, Jr. et al. |
| 6,309,367 B1 | 10/2001 | Boock |
| 6,322,576 B1 | 11/2001 | Wallace et al. |
| 6,344,048 B1 | 2/2002 | Chin et al. |
| 6,346,117 B1 | 2/2002 | Greenhalgh |
| 6,350,270 B1 | 2/2002 | Roue |
| 6,368,339 B1 | 4/2002 | Amplatz |
| 6,371,980 B1 | 4/2002 | Rudakov et al. |
| 6,375,668 B1 | 4/2002 | Gifford et al. |
| 6,379,329 B1 | 4/2002 | Naglreiter et al. |
| 6,383,174 B1 | 5/2002 | Eder |
| 6,391,037 B1 | 5/2002 | Greenhalgh |
| 6,428,558 B1 | 8/2002 | Jones et al. |
| 6,447,531 B1 | 9/2002 | Amplatz |
| 6,451,050 B1 | 9/2002 | Rudakov et al. |
| 6,454,780 B1 | 9/2002 | Wallace |
| 6,494,884 B2 | 12/2002 | Gifford, III et al. |
| 6,506,204 B2 | 1/2003 | Mazzocchi |
| 6,511,468 B1 | 1/2003 | Cragg et al. |
| 6,547,804 B2 | 4/2003 | Porter et al. |
| 6,551,303 B1 | 4/2003 | Van Tassel et al. |
| 6,569,179 B2 | 5/2003 | Teoh et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 | 7/2003 | Palmer et al. |
| 6,591,472 B1 | 7/2003 | Noone et al. |
| 6,592,605 B2 | 7/2003 | Lenker et al. |
| 6,599,308 B2 | 7/2003 | Amplatz |
| 6,602,261 B2 | 8/2003 | Greene, Jr. et al. |
| 6,605,101 B1 | 8/2003 | Schaefer et al. |
| 6,605,102 B1 | 8/2003 | Mazzocchi et al. |
| 6,605,111 B2 | 8/2003 | Bose et al. |
| 6,613,074 B1 | 9/2003 | Mitelberg et al. |
| 6,626,939 B1 | 9/2003 | Burnside et al. |
| 6,635,068 B1 | 10/2003 | Dubrul et al. |
| 6,652,555 B1 | 11/2003 | Vantassel et al. |
| 6,652,556 B1 | 11/2003 | Vantassel et al. |
| 6,666,882 B1 | 12/2003 | Bose et al. |
| 6,669,717 B2 | 12/2003 | Marotta et al. |
| 6,669,721 B1 | 12/2003 | Bose et al. |
| 6,682,546 B2 | 1/2004 | Amplatz |
| 6,689,150 B1 | 2/2004 | Vantassel et al. |
| 6,689,486 B2 | 2/2004 | Ho et al. |
| 6,723,112 B2 | 4/2004 | Ho et al. |
| 6,723,116 B2 | 4/2004 | Taheri |
| 6,730,108 B2 | 5/2004 | Van Tassel et al. |
| 6,746,468 B1 | 6/2004 | Sepetka et al. |
| 6,746,890 B2 | 6/2004 | Gupta et al. |
| 6,780,196 B2 | 8/2004 | Chin et al. |
| 6,802,851 B2 | 10/2004 | Jones et al. |
| 6,811,560 B2 | 11/2004 | Jones et al. |
| 6,855,153 B2 | 2/2005 | Saadat |
| 6,855,154 B2 | 2/2005 | Abdel-gawwad |
| 6,878,384 B2 | 4/2005 | Cruise et al. |
| 6,905,503 B2 | 6/2005 | Gifford, III et al. |
| 6,936,055 B1 | 8/2005 | Ken et al. |
| 6,936,058 B2 | 8/2005 | Forde et al. |
| 6,949,113 B2 | 9/2005 | Van Tassel et al. |
| 6,953,473 B2 | 10/2005 | Porter |
| 6,991,617 B2 | 1/2006 | Hektner et al. |
| 6,994,092 B2 | 2/2006 | Van Der Burg et al. |
| 6,994,717 B2 | 2/2006 | Konya et al. |
| 7,011,671 B2 | 3/2006 | Welch |
| 7,014,645 B2 | 3/2006 | Greene, Jr. et al. |
| 7,029,487 B2 | 4/2006 | Greene, Jr. et al. |
| 7,029,949 B2 | 4/2006 | Farnworth et al. |
| 7,070,609 B2 | 7/2006 | West |
| 7,083,632 B2 | 8/2006 | Avellanet et al. |
| 7,128,073 B1 | 10/2006 | Van Der Burg et al. |
| 7,128,736 B1 | 10/2006 | Abrams et al. |

(56) References Cited

U.S. PATENT DOCUMENTS

| | | |
|---|---|---|
| 7,153,323 B1 | 12/2006 | Teoh et al. |
| 7,169,177 B2 | 1/2007 | Obara |
| 7,195,636 B2 | 3/2007 | Avellanet et al. |
| 7,229,461 B2 | 6/2007 | Chin et al. |
| 7,232,461 B2 | 6/2007 | Ramer |
| 7,306,622 B2 | 12/2007 | Jones et al. |
| 7,326,225 B2 | 2/2008 | Ferrera et al. |
| 7,331,980 B2 | 2/2008 | Dubrul et al. |
| 7,410,482 B2 | 8/2008 | Murphy et al. |
| 7,419,503 B2 | 9/2008 | Pulnev et al. |
| 7,473,266 B2 | 1/2009 | Glaser |
| 7,481,821 B2 | 1/2009 | Fogarty et al. |
| 7,491,214 B2 | 2/2009 | Greene, Jr. et al. |
| 7,569,066 B2 | 8/2009 | Gerberding et al. |
| 7,572,288 B2 | 8/2009 | Cox |
| 7,597,704 B2 | 10/2009 | Frazier et al. |
| 7,601,160 B2 | 10/2009 | Richter |
| 7,608,088 B2 | 10/2009 | Jones et al. |
| 7,695,488 B2 | 4/2010 | Berenstein et al. |
| 7,699,056 B2 | 4/2010 | Tran et al. |
| 7,708,754 B2 | 5/2010 | Balgobin et al. |
| 7,727,189 B2 | 6/2010 | Vantassel et al. |
| 7,744,583 B2 | 6/2010 | Seifert et al. |
| 7,744,652 B2 | 6/2010 | Morsi |
| 7,879,065 B2 | 2/2011 | Gesswein et al. |
| 7,976,527 B2 | 7/2011 | Cragg et al. |
| RE42,625 E | 8/2011 | Guglielmi |
| 7,993,364 B2 | 8/2011 | Morsi |
| RE42,758 E | 9/2011 | Ken et al. |
| 8,012,210 B2 | 9/2011 | Lin et al. |
| 8,043,326 B2 | 10/2011 | Hancock et al. |
| 8,062,379 B2 | 11/2011 | Morsi |
| 8,075,585 B2 | 12/2011 | Lee et al. |
| 8,137,293 B2 | 3/2012 | Zhou et al. |
| 8,142,456 B2 | 3/2012 | Rosqueta et al. |
| 8,202,280 B2 | 6/2012 | Richter |
| 8,211,160 B2 | 7/2012 | Garrison et al. |
| 8,221,445 B2 | 7/2012 | Van Tassel et al. |
| 8,333,783 B2 | 12/2012 | Braun et al. |
| 8,343,167 B2 | 1/2013 | Henson |
| 8,361,104 B2 | 1/2013 | Jones et al. |
| 8,361,138 B2 | 1/2013 | Adams |
| 8,372,062 B2 | 2/2013 | Murphy et al. |
| 8,398,670 B2 | 3/2013 | Amplatz et al. |
| 8,425,541 B2 | 4/2013 | Masters et al. |
| 8,470,013 B2 | 6/2013 | Duggal et al. |
| 8,597,320 B2 | 12/2013 | Sepetka et al. |
| 8,603,128 B2 | 12/2013 | Greene, Jr. et al. |
| 8,690,936 B2 | 4/2014 | Nguyen et al. |
| 8,715,317 B1 | 5/2014 | Janardhan et al. |
| 8,834,515 B2 | 9/2014 | Win et al. |
| 8,906,057 B2 | 12/2014 | Connor et al. |
| 8,974,512 B2 | 3/2015 | Aboytes et al. |
| 8,998,947 B2 | 4/2015 | Aboytes et al. |
| 9,211,202 B2 | 12/2015 | Strother et al. |
| 9,301,769 B2 | 4/2016 | Brady et al. |
| 9,314,248 B2 | 4/2016 | Molaei |
| 9,339,275 B2 | 5/2016 | Trommeter et al. |
| 9,486,224 B2 | 11/2016 | Riina et al. |
| 9,629,636 B2 | 4/2017 | Fogarty et al. |
| 9,713,475 B2 | 7/2017 | Divino et al. |
| 9,833,309 B2 | 12/2017 | Levi et al. |
| 9,844,380 B2 | 12/2017 | Furey |
| 9,907,684 B2 | 3/2018 | Connor et al. |
| 9,918,718 B2 | 3/2018 | Lorenzo |
| 9,962,146 B2 | 5/2018 | Hebert et al. |
| 10,028,745 B2 | 7/2018 | Morsi |
| 10,130,372 B2 | 11/2018 | Griffin |
| 10,932,933 B2 | 3/2021 | Bardsley et al. |
| 10,952,740 B2 | 3/2021 | Dasnurkar et al. |
| 11,076,860 B2 | 8/2021 | Lorenzo |
| 11,134,953 B2 | 10/2021 | Solaun |
| 11,179,159 B2 | 11/2021 | Cox et al. |
| 11,389,309 B2 | 7/2022 | Ruvalcaba et al. |
| 2001/0000797 A1 | 5/2001 | Mazzocchi |
| 2001/0001835 A1 | 5/2001 | Greene et al. |
| 2002/0026210 A1 | 2/2002 | Abdel-gawwad |
| 2002/0042628 A1 | 4/2002 | Chin et al. |
| 2002/0062145 A1 | 5/2002 | Rudakov et al. |
| 2002/0119177 A1 | 8/2002 | Bowman et al. |
| 2002/0147462 A1 | 10/2002 | Mair et al. |
| 2002/0165572 A1 | 11/2002 | Saadat |
| 2002/0169473 A1 | 11/2002 | Sepetka et al. |
| 2002/0193812 A1 | 12/2002 | Patel et al. |
| 2002/0193813 A1 | 12/2002 | Helkowski et al. |
| 2003/0004533 A1 | 1/2003 | Dieck et al. |
| 2003/0004568 A1 | 1/2003 | Ken et al. |
| 2003/0018294 A1 | 1/2003 | Cox |
| 2003/0028209 A1 | 2/2003 | Teoh et al. |
| 2003/0040772 A1 | 2/2003 | Hyodoh et al. |
| 2003/0055440 A1 | 3/2003 | Jones et al. |
| 2003/0065303 A1 | 4/2003 | Wellman et al. |
| 2003/0093111 A1 | 5/2003 | Ken et al. |
| 2003/0113478 A1 | 6/2003 | Dang et al. |
| 2003/0114918 A1 | 6/2003 | Garrison et al. |
| 2003/0149490 A1 | 8/2003 | Ashman |
| 2003/0171739 A1 | 9/2003 | Murphy et al. |
| 2003/0187473 A1 | 10/2003 | Berenstein et al. |
| 2003/0195553 A1 | 10/2003 | Wallace et al. |
| 2003/0212419 A1 | 11/2003 | West |
| 2004/0034386 A1 | 2/2004 | Fulton et al. |
| 2004/0044361 A1 | 3/2004 | Frazier et al. |
| 2004/0044391 A1 | 3/2004 | Porter |
| 2004/0064093 A1 | 4/2004 | Hektner et al. |
| 2004/0098027 A1 | 5/2004 | Teoh et al. |
| 2004/0106945 A1 | 6/2004 | Thramann et al. |
| 2004/0115164 A1 | 6/2004 | Pierce et al. |
| 2004/0122467 A1 | 6/2004 | Vantassel et al. |
| 2004/0138758 A1 | 7/2004 | Kronengold et al. |
| 2004/0161451 A1 | 8/2004 | Pierce et al. |
| 2004/0167597 A1 | 8/2004 | Costantino et al. |
| 2004/0176798 A1 | 9/2004 | Foy et al. |
| 2004/0181253 A1 | 9/2004 | Sepetka et al. |
| 2004/0236344 A1 | 11/2004 | Monstadt et al. |
| 2005/0021077 A1 | 1/2005 | Chin et al. |
| 2005/0038470 A1 | 2/2005 | Van et al. |
| 2005/0049625 A1 | 3/2005 | Shaya et al. |
| 2005/0119684 A1 | 6/2005 | Guterman et al. |
| 2005/0131443 A1 | 6/2005 | Abdel-gawwad |
| 2005/0222580 A1 | 10/2005 | Gifford et al. |
| 2005/0267510 A1 | 12/2005 | Razack |
| 2005/0267511 A1 | 12/2005 | Marks et al. |
| 2005/0267527 A1 | 12/2005 | Sandoval et al. |
| 2005/0277978 A1 | 12/2005 | Greenhalgh |
| 2005/0278023 A1 | 12/2005 | Zwirkoski |
| 2006/0028209 A1 | 2/2006 | Walker |
| 2006/0034883 A1 | 2/2006 | Dang et al. |
| 2006/0052816 A1 | 3/2006 | Bates et al. |
| 2006/0064151 A1 | 3/2006 | Guterman et al. |
| 2006/0106421 A1 | 5/2006 | Teoh |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0116714 A1 | 6/2006 | Sepetka et al. |
| 2006/0122548 A1 | 6/2006 | Abrams |
| 2006/0155323 A1 | 7/2006 | Porter et al. |
| 2006/0190070 A1 | 8/2006 | Dieck et al. |
| 2006/0200234 A1 | 9/2006 | Hines |
| 2006/0206140 A1 | 9/2006 | Shaolian et al. |
| 2006/0206198 A1 | 9/2006 | Churchwell et al. |
| 2006/0206199 A1 | 9/2006 | Churchwell et al. |
| 2006/0241686 A1 | 10/2006 | Ferrera et al. |
| 2006/0247680 A1 | 11/2006 | Amplatz et al. |
| 2006/0271162 A1 | 11/2006 | Vito et al. |
| 2006/0276824 A1 | 12/2006 | Mitelberg et al. |
| 2006/0276829 A1 | 12/2006 | Balgobin et al. |
| 2006/0276830 A1 | 12/2006 | Balgobin et al. |
| 2007/0003594 A1 | 1/2007 | Brady et al. |
| 2007/0010850 A1 | 1/2007 | Balgobin et al. |
| 2007/0014831 A1 | 1/2007 | Sung et al. |
| 2007/0083226 A1 | 4/2007 | Buiser et al. |
| 2007/0100426 A1 | 5/2007 | Rudakov et al. |
| 2007/0135907 A1 | 6/2007 | Wilson et al. |
| 2007/0167876 A1 | 7/2007 | Euteneuer et al. |

(56) References Cited

U.S. PATENT DOCUMENTS

| | | |
|---|---|---|
| 2007/0167877 A1 | 7/2007 | Euteneuer et al. |
| 2007/0167972 A1 | 7/2007 | Euteneuer et al. |
| 2007/0175536 A1 | 8/2007 | Monetti et al. |
| 2007/0179507 A1 | 8/2007 | Shah |
| 2007/0179520 A1 | 8/2007 | West |
| 2007/0185442 A1 | 8/2007 | Euteneuer et al. |
| 2007/0185443 A1 | 8/2007 | Euteneuer et al. |
| 2007/0185444 A1 | 8/2007 | Euteneuer et al. |
| 2007/0185457 A1 | 8/2007 | Euteneuer et al. |
| 2007/0186933 A1 | 8/2007 | Domingo et al. |
| 2007/0191924 A1 | 8/2007 | Rudakov |
| 2007/0198059 A1 | 8/2007 | Patel et al. |
| 2007/0198075 A1 | 8/2007 | Levy |
| 2007/0219619 A1 | 9/2007 | Dieck et al. |
| 2007/0221230 A1 | 9/2007 | Thompson et al. |
| 2007/0265656 A1 | 11/2007 | Amplatz et al. |
| 2007/0270902 A1 | 11/2007 | Slazas et al. |
| 2007/0276426 A1 | 11/2007 | Euteneuer |
| 2007/0276427 A1 | 11/2007 | Euteneuer |
| 2007/0282373 A1 | 12/2007 | Ashby et al. |
| 2007/0288083 A1 | 12/2007 | Hines |
| 2007/0299461 A1 | 12/2007 | Elliott |
| 2008/0033366 A1 | 2/2008 | Matson et al. |
| 2008/0065145 A1 | 3/2008 | Carpenter |
| 2008/0081763 A1 | 4/2008 | Swetlin et al. |
| 2008/0082176 A1 | 4/2008 | Slazas |
| 2008/0086196 A1 | 4/2008 | Truckai et al. |
| 2008/0109057 A1 | 5/2008 | Calabria et al. |
| 2008/0114391 A1 | 5/2008 | Dieck et al. |
| 2008/0114436 A1 | 5/2008 | Dieck et al. |
| 2008/0119886 A1 | 5/2008 | Greenhalgh et al. |
| 2008/0125852 A1 | 5/2008 | Garrison et al. |
| 2008/0132820 A1 | 6/2008 | Buckman et al. |
| 2008/0140177 A1 | 6/2008 | Hines |
| 2008/0200945 A1 | 8/2008 | Amplatz et al. |
| 2008/0200979 A1 | 8/2008 | Dieck et al. |
| 2008/0221554 A1 | 9/2008 | Oconnor et al. |
| 2008/0221600 A1 | 9/2008 | Dieck et al. |
| 2008/0221703 A1 | 9/2008 | Que et al. |
| 2008/0281350 A1 | 11/2008 | Sepetka et al. |
| 2008/0283066 A1 | 11/2008 | Delgado et al. |
| 2009/0018637 A1 | 1/2009 | Paul, Jr. et al. |
| 2009/0024224 A1 | 1/2009 | Chen et al. |
| 2009/0025820 A1 | 1/2009 | Adams |
| 2009/0036877 A1 | 2/2009 | Nardone et al. |
| 2009/0043375 A1 | 2/2009 | Rudakov et al. |
| 2009/0056722 A1 | 3/2009 | Swann |
| 2009/0062899 A1 | 3/2009 | Dang et al. |
| 2009/0076540 A1 | 3/2009 | Marks et al. |
| 2009/0099592 A1 | 4/2009 | Buiser et al. |
| 2009/0112249 A1 | 4/2009 | Miles et al. |
| 2009/0112251 A1 | 4/2009 | Qian et al. |
| 2009/0125119 A1 | 5/2009 | Obermiller et al. |
| 2009/0148492 A1 | 6/2009 | Dave et al. |
| 2009/0155367 A1 | 6/2009 | Neuwirth et al. |
| 2009/0187214 A1 | 7/2009 | Amplatz et al. |
| 2009/0264978 A1 | 10/2009 | Dieck et al. |
| 2009/0270974 A1 | 10/2009 | Berez et al. |
| 2009/0275974 A1 | 11/2009 | Marchand et al. |
| 2009/0287291 A1 | 11/2009 | Becking et al. |
| 2009/0287292 A1 | 11/2009 | Becking et al. |
| 2009/0287294 A1 | 11/2009 | Rosqueta et al. |
| 2009/0287297 A1 | 11/2009 | Cox |
| 2009/0297582 A1 | 12/2009 | Meyer et al. |
| 2009/0306702 A1 | 12/2009 | Miloslavski et al. |
| 2009/0318892 A1 | 12/2009 | Aboytes et al. |
| 2009/0318941 A1 | 12/2009 | Sepetka et al. |
| 2009/0319023 A1 | 12/2009 | Hildebrand et al. |
| 2010/0023048 A1 | 1/2010 | Mach |
| 2010/0030200 A1 | 2/2010 | Strauss et al. |
| 2010/0036410 A1 | 2/2010 | Krolik et al. |
| 2010/0106178 A1 | 4/2010 | Obermiller et al. |
| 2010/0121350 A1 | 5/2010 | Mirigian |
| 2010/0131002 A1 | 5/2010 | Connor et al. |
| 2010/0139465 A1 | 6/2010 | Christian et al. |
| 2010/0144895 A1 | 6/2010 | Porter |
| 2010/0160949 A1 | 6/2010 | Takuma |
| 2010/0174269 A1 | 7/2010 | Tompkins et al. |
| 2010/0185271 A1 | 7/2010 | Zhang |
| 2010/0228184 A1 | 9/2010 | Mavani et al. |
| 2010/0249830 A1 | 9/2010 | Nelson |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0262014 A1 | 10/2010 | Huang |
| 2010/0268201 A1 | 10/2010 | Tieu et al. |
| 2010/0274276 A1 | 10/2010 | Chow et al. |
| 2010/0298791 A1 | 11/2010 | Jones et al. |
| 2010/0312061 A1 | 12/2010 | Hess et al. |
| 2011/0022149 A1 | 1/2011 | Cox et al. |
| 2011/0046658 A1 | 2/2011 | Connor et al. |
| 2011/0077620 A1 | 3/2011 | Debeer |
| 2011/0125110 A1 | 5/2011 | Cotton |
| 2011/0137332 A1 | 6/2011 | Sepetka et al. |
| 2011/0137405 A1 | 6/2011 | Wilson et al. |
| 2011/0144669 A1 | 6/2011 | Becking et al. |
| 2011/0152993 A1 | 6/2011 | Marchand et al. |
| 2011/0166588 A1 | 7/2011 | Connor et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0224776 A1 | 9/2011 | Sepetka et al. |
| 2011/0238041 A1 | 9/2011 | Lim et al. |
| 2011/0245862 A1 | 10/2011 | Dieck et al. |
| 2011/0251699 A1 | 10/2011 | Ladet |
| 2011/0265943 A1 | 11/2011 | Rosqueta et al. |
| 2011/0319926 A1 | 12/2011 | Becking et al. |
| 2012/0010644 A1 | 1/2012 | Sideris et al. |
| 2012/0022572 A1 | 1/2012 | Braun et al. |
| 2012/0041472 A1 | 2/2012 | Tan et al. |
| 2012/0101510 A1 | 4/2012 | Lenker et al. |
| 2012/0116350 A1 | 5/2012 | Strauss et al. |
| 2012/0123510 A1 | 5/2012 | Liungman |
| 2012/0143237 A1 | 6/2012 | Cam et al. |
| 2012/0143243 A1 | 6/2012 | Hill et al. |
| 2012/0143301 A1 | 6/2012 | Maslanka et al. |
| 2012/0165919 A1 | 6/2012 | Cox et al. |
| 2012/0197283 A1 | 8/2012 | Marchand et al. |
| 2012/0239074 A1 | 9/2012 | Aboytes et al. |
| 2012/0283768 A1 | 11/2012 | Cox et al. |
| 2012/0283769 A1 | 11/2012 | Cruise et al. |
| 2012/0310269 A1 | 12/2012 | Fearnot et al. |
| 2012/0316598 A1 | 12/2012 | Becking et al. |
| 2012/0316632 A1 | 12/2012 | Gao |
| 2012/0323271 A1 | 12/2012 | Obermiller et al. |
| 2012/0330341 A1 | 12/2012 | Becking et al. |
| 2012/0330347 A1 | 12/2012 | Becking et al. |
| 2012/0330348 A1 | 12/2012 | Strauss et al. |
| 2013/0066357 A1 | 3/2013 | Aboytes et al. |
| 2013/0066360 A1 | 3/2013 | Becking et al. |
| 2013/0073026 A1 | 3/2013 | Russo et al. |
| 2013/0085522 A1 | 4/2013 | Becking et al. |
| 2013/0116722 A1 | 5/2013 | Aboytes et al. |
| 2013/0138136 A1 | 5/2013 | Beckham et al. |
| 2013/0211495 A1 | 8/2013 | Halden et al. |
| 2013/0274866 A1 | 10/2013 | Cox et al. |
| 2014/0012307 A1 | 1/2014 | Franano et al. |
| 2014/0039542 A1 | 2/2014 | Trommeter et al. |
| 2014/0058420 A1 | 2/2014 | Hannes et al. |
| 2014/0135810 A1 | 5/2014 | Divino et al. |
| 2014/0135811 A1 | 5/2014 | Divino et al. |
| 2014/0135812 A1 | 5/2014 | Divino et al. |
| 2014/0200607 A1 | 7/2014 | Sepetka et al. |
| 2014/0215792 A1 | 8/2014 | Leopold et al. |
| 2014/0257360 A1 | 9/2014 | Keillor |
| 2014/0257361 A1 | 9/2014 | Prom |
| 2014/0316012 A1 | 10/2014 | Freyman et al. |
| 2014/0371734 A1 | 12/2014 | Truckai |
| 2014/0377187 A1 | 12/2014 | Lerouge et al. |

(56) References Cited

U.S. PATENT DOCUMENTS

| | | |
|---|---|---|
| 2015/0005808 A1 | 1/2015 | Chouinard et al. |
| 2015/0216684 A1 | 8/2015 | Enzmann et al. |
| 2015/0250628 A1 | 9/2015 | Monstadt et al. |
| 2015/0272589 A1 | 10/2015 | Lorenzo |
| 2015/0272590 A1 | 10/2015 | Aboytes et al. |
| 2015/0313605 A1 | 11/2015 | Griffin |
| 2015/0313737 A1 | 11/2015 | Tippett et al. |
| 2015/0327843 A1 | 11/2015 | Garrison |
| 2015/0335333 A1 | 11/2015 | Jones et al. |
| 2015/0342613 A1 | 12/2015 | Aboytes et al. |
| 2015/0343181 A1 | 12/2015 | Bradway et al. |
| 2016/0022445 A1 | 1/2016 | Ruvalcaba et al. |
| 2016/0030050 A1 | 2/2016 | Franano et al. |
| 2016/0066921 A1 | 3/2016 | Seifert et al. |
| 2016/0106437 A1 | 4/2016 | Van Der Burg et al. |
| 2016/0128699 A1 | 5/2016 | Hadley et al. |
| 2016/0135984 A1 | 5/2016 | Rudakov et al. |
| 2016/0206320 A1 | 7/2016 | Connor |
| 2016/0206321 A1 | 7/2016 | Connor |
| 2016/0256170 A1 | 9/2016 | Busold et al. |
| 2016/0331381 A1 | 11/2016 | Ma |
| 2017/0105739 A1 | 4/2017 | Dias et al. |
| 2017/0150971 A1 | 6/2017 | Hines |
| 2017/0156734 A1 | 6/2017 | Griffin |
| 2017/0156903 A1 | 6/2017 | Shobayashi |
| 2017/0189035 A1 | 7/2017 | Porter |
| 2017/0224350 A1 | 8/2017 | Shimizu et al. |
| 2017/0224355 A1 | 8/2017 | Bowman et al. |
| 2017/0266023 A1 | 9/2017 | Thomas |
| 2017/0340333 A1 | 11/2017 | Badruddin et al. |
| 2017/0354421 A1 | 12/2017 | Maguire et al. |
| 2017/0367708 A1 | 12/2017 | Mayer et al. |
| 2017/0367713 A1 | 12/2017 | Greene et al. |
| 2018/0049859 A1 | 2/2018 | Stoppenhagen et al. |
| 2018/0070955 A1 | 3/2018 | Greene et al. |
| 2018/0110797 A1 | 4/2018 | Li et al. |
| 2018/0125686 A1 | 5/2018 | Lu |
| 2018/0132856 A1 | 5/2018 | Wierzbicki et al. |
| 2018/0140305 A1 | 5/2018 | Connor |
| 2018/0161185 A1 | 6/2018 | Kresslein et al. |
| 2018/0193025 A1 | 7/2018 | Walzman |
| 2018/0193026 A1 | 7/2018 | Yang et al. |
| 2018/0206852 A1 | 7/2018 | Moeller |
| 2018/0242979 A1 | 8/2018 | Lorenzo |
| 2018/0256171 A1 | 9/2018 | Chow et al. |
| 2018/0317932 A1 | 11/2018 | H'Doubler |
| 2019/0008522 A1 | 1/2019 | Lorenzo |
| 2019/0009057 A1 | 1/2019 | Li et al. |
| 2019/0053807 A1 | 2/2019 | Tassoni et al. |
| 2019/0053811 A1 | 2/2019 | Garza et al. |
| 2019/0223876 A1 | 7/2019 | Badruddin et al. |
| 2019/0223881 A1 | 7/2019 | Hewitt et al. |
| 2019/0282242 A1 | 9/2019 | Divino et al. |
| 2019/0343532 A1 | 11/2019 | Divino et al. |
| 2019/0351107 A1 | 11/2019 | Sawhney et al. |
| 2020/0061099 A1 | 2/2020 | Li et al. |
| 2020/0138448 A1 | 5/2020 | Dasnurkar et al. |
| 2020/0268392 A1 | 8/2020 | Choi et al. |
| 2021/0128160 A1 | 5/2021 | Li et al. |
| 2021/0128161 A1 | 5/2021 | Nageswaran et al. |
| 2021/0128165 A1 | 5/2021 | Pulugurtha et al. |
| 2021/0128167 A1 | 5/2021 | Patel et al. |
| 2021/0128168 A1 | 5/2021 | Nguyen et al. |
| 2021/0128169 A1 | 5/2021 | Li et al. |
| 2021/0129275 A1 | 5/2021 | Nguyen et al. |
| 2021/0153872 A1 | 5/2021 | Nguyen et al. |
| 2021/0161643 A1 | 6/2021 | Totten et al. |
| 2021/0196284 A1 | 7/2021 | Gorochow et al. |
| 2021/0212698 A1 | 7/2021 | Connor |

FOREIGN PATENT DOCUMENTS

| | | |
|---|---|---|
| CN | 102083493 A | 6/2011 |
| CN | 102202585 A | 9/2011 |
| CN | 202313544 U | 7/2012 |
| CN | 102740799 A | 10/2012 |
| CN | 105105812 A | 12/2015 |
| CN | 105209075 A | 12/2015 |
| DE | 102011102933 A1 | 12/2012 |
| EP | 0717969 A2 | 6/1996 |
| EP | 1188414 A1 | 3/2002 |
| EP | 1813213 A2 | 8/2007 |
| EP | 2208483 A1 | 7/2010 |
| EP | 2468348 B1 | 10/2016 |
| JP | 2005261951 A | 9/2005 |
| JP | 2008521492 A | 6/2008 |
| WO | WO 9406502 A2 | 3/1994 |
| WO | WO 9905977 A1 | 2/1999 |
| WO | WO 03011151 A1 | 2/2003 |
| WO | WO 2006034149 A2 | 3/2006 |
| WO | WO 2007006139 A1 | 1/2007 |
| WO | 2007079402 A2 | 7/2007 |
| WO | WO 2007121405 A2 | 10/2007 |
| WO | WO 2008074027 A1 | 6/2008 |
| WO | WO 2009014528 A1 | 1/2009 |
| WO | WO 2009134337 A1 | 11/2009 |
| WO | WO 2010009019 A1 | 1/2010 |
| WO | WO 2010027363 A1 | 3/2010 |
| WO | WO 2010028300 A1 | 3/2010 |
| WO | WO 2010077599 A1 | 7/2010 |
| WO | WO 2011066962 A1 | 6/2011 |
| WO | WO 2011095966 A1 | 8/2011 |
| WO | WO 2012034135 A1 | 3/2012 |
| WO | WO 2013112944 A1 | 8/2013 |
| WO | WO 2013138615 A2 | 9/2013 |
| WO | WO 2013138615 A3 | 9/2014 |
| WO | 2014169708 A1 | 10/2014 |
| WO | 2015160721 A1 | 10/2015 |
| WO | 2015166013 A1 | 11/2015 |
| WO | WO 2017074411 A1 | 5/2017 |
| WO | 2018050262 A1 | 3/2018 |
| WO | WO 2018051187 A1 | 3/2018 |
| WO | 2019038293 A1 | 2/2019 |

OTHER PUBLICATIONS

Berenstein et al., Treatment of Experimental Aneurysms With an Embolic-Containing Device and Liquid Embolic Agent: Feasibility and Angiographic and Histological Results, Neurosurgery, vol. 64, No. 2, Feb. 2009, 367-373.

Brennecka et al., In vivo embolization of lateral wall aneurysms in canines using the liquid-to-solid gelling PPODA-QT polymer system: 6-month pilot study, J Neurosurg, Apr. 5, 2013, pp. 1-11.

Brennecka et al., In Vivo Experimental Aneurysm Embolization in a Swine Model with a Liquid-to-Solid Gelling Polymer System: Initial Biocompatibility and Delivery Strategy Analysis, World Neurosurgeiy 78[5]: 469-480, Nov. 2012.

Jalani et al., Tough, in-situ thermogelling, injectable hydrogels for biomedical applications, Macromol Biosci. Apr. 2015;15(4):473-80, [Abstract only].

Murayama, et al., Endovascular Treatment of Experimental Aneurysms by Use of a Combination of Liquid Embolic Agents and Protective Devices, AJNR Am J Neuroradiol 21:1726-1735, Oct. 2000.

Ning et al., Experimental study of temperature-sensitive chitosan/ β-glycerophosphate embolic material in embolizing the basicranial rete mirabile in swines, Experimental and Therapeutic Medicine 10: 316-322, 2015.

Nonn et al., Feasibility, Safety, and Efficacy of Flow-Diverting Stent-Assisted Microsphere Embolization of Fusiform and Sidewall Aneurysms, www.neurosurgery-online.com, vol. 77, No. 1, Jul. 2015, 11 pages.

Wang et al., In Vivo Assessment of Chitosan/β-Glycerophosphate as a New Liquid Embolic Agent, Interventional Neuroradiology 17: 87-92, 2011.

Zhen et al., Embolization of aneurysm by chitosan-glycerophosphate-fibroblast tissue hydrogel, a tissue engineering material: experiment with rabbits, Nail Med J China, Mar. 24, 2009, Vo. 89, No. 11, [Abstract only].

(56) References Cited

OTHER PUBLICATIONS

Molyneux, et al., International Subarachnoid Aneurysm Trial (ISAT) of neurosurgical clipping versus endovascular coiling in 2143 patients with ruptured intracranial aneurysms: a randomised trial, Lancet 2002; 360: 1267-74.

Murayama, et al., Guglielmi Detachable Coil embolization of cerebral aneurysms: 11 years' experience, J Neurosurg 98:959-966, 2003.

International Search Report and Written Opinion dated Feb. 17, 2021, International Application No. PCT/US20/70741, 6 pages.

International Search Report and Written Opinion dated Feb. 23, 2021, International Application No. PCT/US20/70743, 14 pages.

International Search Report and Written Opinion dated Apr. 13, 2021, International Application No. PCT/US20/70742, 18 pages.

DEVICES, SYSTEMS, AND METHODS FOR TREATMENT OF INTRACRANIAL ANEURYSMS

CROSS-REFERENCE TO RELATED APPLICATION(S)

The present application claims the benefit of priority of U.S. Provisional Application No. 62/930,421, filed Nov. 4, 2019, U.S. Provisional Application No. 62/930,487, filed Nov. 4, 2019, U.S. Provisional Application No. 62/930,303, filed Nov. 4, 2019, U.S. Provisional Application No. 62/930,324, filed Nov. 4, 2019, U.S. Provisional Application No. 62/930,333, filed Nov. 4, 2019, and U.S. Provisional Application No. 62/930,357, filed Nov. 4, 2019, each of which is incorporated by reference herein in its entirety.

The following applications are also incorporated by reference herein in their entireties: U.S. patent application Ser. No. 16/949,567, filed Nov. 3, 2020, and titled DEVICES, SYSTEMS, AND METHODS FOR TREATMENT OF INTRACRANIAL ANEURYSMS; U.S. patent application Ser. No. 16/949,561, filed Nov. 3, 2020, and titled SYSTEMS AND METHODS FOR TREATING ANEURYSMS; U.S. patent application Ser. No. 16/949,563, filed Nov. 3, 2020, and titled SYSTEMS AND METHODS FOR TREATING ANEURYSMS; U.S. patent application Ser. No. 16/949,564, filed Nov. 3, 2020, and titled SYSTEMS AND METHODS FOR TREATING ANEURYSMS; U.S. patent application Ser. No. 16/949,565, filed Nov. 3, 2020, and titled SYSTEMS AND METHODS FOR TREATING ANEURYSMS; U.S. patent application Ser. No. 16/949,569, filed Nov. 3, 2020, and titled DEVICES, SYSTEMS, AND METHODS FOR TREATMENT OF INTRACRANIEL ANEURYSMS; U.S. patent application Ser. No. 16/949,566, filed Nov. 3, 2020, and titled SYSTEMS AND METHODS FOR TREATING ANEURYSMS; U.S. patent application Ser. No. 16/949,570, filed Nov. 3, 2020, and titled DEVICES, SYSTEMS, AND METHODS FOR TREATING ANEURYSMS; International Application No PCT/US2020/070743, filed Nov. 3, 2020, titled DEVICES, SYSTEMS, AND METHODS FOR TREATMENT OF INTRACRANIAL ANEURYSMS; International Application No. PCT/US2020/070741, filed Nov. 3, 2020, titled DEVICES, SYSTEMS, AND METHODS FOR TREATMENT OF INTRACRANIAL ANEURYSMS; and International Application No. PCT/US2020/070742, filed Nov. 3, 2020, titled SYSTEMS AND METHODS FOR TREATING ANEURYSMS.

TECHNICAL FIELD

The present technology relates to systems, devices, and methods for treating intracranial aneurysms.

BACKGROUND

An intracranial aneurysm is a portion of an intracranial blood vessel that bulges outward from the blood vessel's main channel. This condition often occurs at a portion of a blood vessel that is abnormally weak because of a congenital anomaly, trauma, high blood pressure, or for another reason. Once an intracranial aneurysm forms, there is a significant risk that the aneurysm will eventually rupture and cause a medical emergency with a high risk of mortality due to hemorrhaging. When an unruptured intracranial aneurysm is detected or when a patient survives an initial rupture of an intracranial aneurysm, vascular surgery is often indicated.

One conventional type of vascular surgery for treating an intracranial aneurysm includes using a microcatheter to dispose a platinum coil within an interior volume of the aneurysm. Over time, the presence of the coil should induce formation of a thrombus. Ideally, the aneurysm's neck closes at the site of the thrombus and is replaced with new endothelial tissue. Blood then bypasses the aneurysm, thereby reducing the risk of aneurysm rupture (or re-rupture) and associated hemorrhaging. Unfortunately, long-term recanalization (i.e., restoration of blood flow to the interior volume of the aneurysm) after this type of vascular surgery occurs in a number of cases, especially for intracranial aneurysms with relatively wide necks and/or relatively large interior volumes.

Another conventional type of vascular surgery for treating an intracranial aneurysm includes deploying a flow diverter within the associated intracranial blood vessel. The flow diverter is often a mesh tube that causes blood to preferentially flow along a main channel of the blood vessel while blood within the aneurysm stagnates. The stagnant blood within the aneurysm should eventually form a thrombus that leads to closure of the aneurysm's neck and to growth of new endothelial tissue, as with the platinum coil treatment. One significant drawback of flow diverters is that it may take weeks or months to form aneurysmal thrombus and significantly longer for the aneurysm neck to be covered with endothelial cells for full effect. This delay may be unacceptable when risk of aneurysm rupture (or re-rupture) is high. Moreover, flow diverters typically require antiplatelet therapy to prevent a thrombus from forming within the main channel of the blood vessel at the site of the flow diverter. Antiplatelet therapy may be contraindicated shortly after an initial aneurysm rupture has occurred because risk of re-rupture at this time is high and antiplatelet therapy tends to exacerbate intracranial hemorrhaging if re-rupture occurs. For these and other reasons, there is a need for innovation in the treatment of intracranial aneurysms. Given the severity of this condition, innovation in this field has immediate life-saving potential.

SUMMARY

The subject technology is illustrated, for example, according to various aspects described below, including with reference to FIGS. 1A-7J. Various examples of aspects of the subject technology are described as numbered clauses (1, 2, 3, etc.) for convenience. These are provided as examples and do not limit the subject technology.

1. A method for treating an aneurysm, the method comprising:
   positioning a distal end of an elongated shaft in an aneurysm cavity;
   releasing an occlusive member from the elongated shaft while the distal end of the elongated shaft is positioned within the aneurysm cavity such that the occlusive member self-expands to assume a first expanded state in which the occlusive member forms a first shape, wherein, in the first expanded state, the occlusive member encloses an interior region having a first interior volume; and
   delivering an embolic element between the occlusive member and the aneurysm wall to transform the occlusive member into a second expanded state in which the occlusive member defines a second interior volume less than the first interior volume, wherein the occlusive member forms a second shape in the second expanded state that is different than the first shape in the first expanded state.

2. The method of any one of the previous Clauses, wherein transforming the occlusive member into the second expanded shape includes injecting the embolic material to urge a portion of a sidewall of the expandable mesh in a direction away from a wall of the aneurysm and towards the interior region of the occlusive member.

3. The method of any one of the previous Clauses, wherein transforming the occlusive member into the second expanded shape includes injecting the embolic material to invert a portion of a sidewall of the occlusive member such that the portion is convex towards the aneurysm wall in the first expanded state and concave towards the aneurysm wall in the second expanded state.

4. The method of any one of the previous Clauses, wherein the embolic element comprises a liquid embolic.

5. The method of any one of the previous Clauses, wherein the embolic element comprises one or more embolization coils.

6. The method of any one of the previous Clauses, wherein delivering the embolic element occurs after the occlusive member is in the first expanded state.

7. The method of any one of the preceding Clauses, wherein the occlusive member is a mesh.

8. The method of any one of the preceding Clauses, wherein the occlusive member is a braid.

9. The method of any one of the preceding Clauses, wherein the occlusive member is a dual-layered braid.

10. The method of any one of the preceding Clauses, wherein the occlusive member has a globular or generally spherical shape in the first expanded state.

11. The method of any one of the preceding Clauses, wherein the occlusive member is cup or bowl-shaped in the second expanded state.

12. The method of any one of the preceding Clauses, wherein the second shape is a predetermined three-dimensional shape.

13. The method of any one of the preceding Clauses, wherein the occlusive member forms a multi-layer braid at the neck of the aneurysm in the second expanded state.

14. The method of any one of the previous Clauses, wherein the occlusive member comprises a plurality of braided filaments that assume a pre-set, three-dimensional shape in the expanded state.

15. The method of any one of the previous Clauses, wherein the occlusive member comprises a braid formed of 24, 32, 36, 48, 64, or 72 filaments.

16. The method of any one of the previous Clauses, wherein the occlusive member comprises a braid formed of a plurality of wires, some or all of which have a diameter of about 0.001 inches (0.00254 cm).

17. The method of any one of the previous Clauses, wherein the occlusive member comprises a braid formed of a plurality of wires, some or all of which have the same diameter.

18. The method of any one of the previous Clauses, wherein the occlusive member comprises a braid formed of a plurality of wires, at least some of which have different diameters.

19. The method of any one of the previous Clauses, wherein the occlusive member forms a closed, globular shape in the expanded state, the mesh having an aperture at a distal portion.

20. The method of any one of the previous Clauses, wherein, in the expanded state, the occlusive member forms one of a sphere, a prolate spheroid, or an oblate spheroid.

21. The method of any one of the previous Clauses, wherein the occlusive member comprises an inner layer and an outer layer.

22. The method of any one of the previous Clauses, wherein the occlusive member comprises an inner layer and an outer layer that meet at a fold at a distal portion of the occlusive member.

23. The method of Clause 22, wherein the expandable mesh includes an aperture at a distal portion, the aperture being defined by the fold.

24. The method of any one of the previous Clauses, wherein the occlusive member comprises an inner layer and an outer layer that meet at a fold at a proximal portion of the occlusive member.

25. The method of Clause 24, wherein the expandable mesh includes an aperture at a distal portion, the aperture being defined by the fold.

26. The method of any one of the previous Clauses, wherein the occlusive member has a maximum cross-sectional dimension of 3.0 mm, 3.5 mm, 4.0 mm, 4.5 mm, 5.0 mm, 5.5 mm, 6.0 mm, 6.5 mm, 7.0 mm, 7.5 mm, or 8.0 mm.

27. The method of any one of the previous Clauses, wherein the occlusive member is formed of a plurality of filaments having first and second ends fixed at a coupler.

28. The method of any one of the previous Clauses, wherein the occlusive member is formed of a plurality of filaments formed of an inner core material surrounded by an outer material.

29. The method of Clause 28, wherein the inner core material is a radiopaque material and the outer material is a superelastic material.

30. The method of any one of the previous Clauses, wherein the occlusive member is a laser-cut tube.

31. The method of any one of the previous Clauses, wherein the occlusive member comprises a plurality of filaments.

32. The method of Clause 31, wherein the filaments are interwoven.

33. The method of Clause 31 or Clause 32, wherein the filaments are braided.

34. The method of any one of Clauses 31 to 33, wherein each of the filaments has a first end and a second end opposite the first end, and wherein both the first and second ends of the filaments are fixed relative to one another at a coupler.

35. The method of Clause 34, wherein the coupler is disposed at a distal end of the occlusive member.

36. The method of Clause 34, wherein the coupler is disposed at a proximal end of the occlusive member.

37. The method of any one of Clauses 31 to 36, wherein each of the filaments terminate at only one end of the occlusive member.

38. The method of Clause 37, wherein the filaments form an opening at an end of the occlusive member opposite the only one end.

39. The method of Clause 38, wherein an inverted portion of each of the filaments define the opening.

40. The method of Clause 39, wherein the inverted portions of the filaments are configured to move relative to one another.

41. The method of any one of the previous Clauses, wherein the embolic element comprises a biopolymer and a chemical crosslinking agent.

42. The method of Clause 42, wherein the biopolymer includes chitosan, a derivative of chitosan, an analog of chitosan, or a combination thereof.

43. The method of Clause 42 or Clause 43, wherein the chemical crosslinking agent includes genipin, a derivative of genipin, an analog of genipin, or a combination thereof.

44. The method of any one of Clauses 42 to 44, wherein the embolic element further comprises a physical crosslinking agent.

45. The method of Clause 45, the physical crosslinking agent includes β glycerophosphate, a derivative of β glycerophosphate, an analog of β glycerophosphate, or a combination thereof.

46. The method of Clause 42, wherein
the biopolymer includes chitosan, a derivative of chitosan, an analog of chitosan, or a combination thereof;
the chemical crosslinking agent includes genipin, a derivative of genipin, an analog of genipin, or a combination thereof; and
the physical crosslinking agent includes β glycerophosphate, a derivative of β glycerophosphate, an analog of β glycerophosphate, or a combination thereof.

47. The method of any one of the preceding Clauses, wherein the embolic element comprises a contrast agent.

48. The method of Clause 48, wherein the contrast agent is selected to provide diminishing radiopacity.

49. The method of Clause 48 or Clause 49, wherein the contrast agent includes iohexol, a derivative of iohexol, an analog of iohexol, or a combination thereof.

50. A method for treating an aneurysm, the method comprising: positioning an expandable occlusive member in an initial expanded state within an
aneurysm, wherein in the initial expanded state the expandable occlusive member
provides a number of layers across a neck of the aneurysm; and doubling the number of layers of the occlusive device across the neck of the aneurysm by
introducing an embolic element to the aneurysm cavity.

51. The method of Clause 51, wherein the number of layers is one.

52. The method of Clause 51, wherein the number of layers is two.

53. The method of any one of Clauses 51 to 53, wherein the layers are mesh layers.

54. The method of any one of Clauses 51 to 54, wherein the occlusive member has a first shape in the initial expanded state, and wherein introducing the embolic element transforms the occlusive member from the initial expanded state to a secondary expanded state in which the occlusive member forms a second shape different than the first shape.

55. The method of Clause 55, wherein a volume enclosed by the first shape is greater than a volume enclosed by the second shape.

56. A method for imaging treatment of an aneurysm, the method comprising:
acquiring a first image visualizing:
an occlusive member positioned within an aneurysm, the occlusive member including a first radiopaque marker; and
a conduit having a distal portion positioned within an aneurysm, the distal portion of the conduit including a second radiopaque marker; and
acquiring a second image in which the first radiopaque marker is further from the second radiopaque marker than in the first image.

57. The method of Clause 56, wherein, in the second image, the first radiopaque marker is positioned proximal to the second radiopaque marker.

58. The method of one of Clauses 56 to 57, wherein, in the second image, the first radiopaque marker is positioned closer to a neck of the aneurysm than in the first image.

59. The method of any one of Clauses 56 to 58, wherein, in the first image, the first radiopaque marker is positioned in a distal half of the occlusive member.

60. The method of any one of Clauses 56 to 59, wherein, in the first image, the first radiopaque marker is positioned on a distal-facing surface of the occlusive member.

61. The method of any one of Clauses 56 to 60, wherein, in the first image, the first radiopaque is positioned proximal to second radiopaque marker.

62. The method of any one of Clauses 56 to 61, wherein, in the first image and in the second image, the second radiopaque marker is disposed nearer to a dome of the aneurysm than the first radiopaque marker.

63. The method of any one of Clauses 56 to 62, wherein, in the second image, a radiopaque occlusive element is visible in a space between the first radiopaque marker and the second radiopaque marker.

64. The method of any one of Clauses 56 to 63, further comprising acquiring a third image in which the first radiopaque marker is further from the second radiopaque marker than in the second image.

65. The method of any one of Clauses 56 to 64, wherein acquiring the first image and acquiring the second image each comprises acquiring a fluoroscopic image.

66. A method for treating an aneurysm, the method comprising:
positioning a distal end of an elongated shaft at or near an aneurysm cavity, the distal end of the shaft containing an occlusive member detachably coupled to an elongated member slidably disposed within the elongated shaft, wherein a distal end of the occlusive member is coupled to a distal end of the elongated member and a proximal end of the occlusive member is slidable over the elongated member;
pushing the elongated member distally from a distal opening in the elongated shaft to pull a distal end of the occlusive member distally through the distal opening to expel the occlusive member from the shaft and allow the occlusive member to self-expand to a first expanded state;
while the occlusive member is in the first expanded state, pulling the elongated member proximally to bring a distal wall of the occlusive member towards a proximal wall of the occlusive member such that the occlusive member forms a second expanded state in which at least a portion of the occlusive member is inverted; and
delivering an embolic element through the elongated member to a position between the occlusive member and the aneurysm wall.

67. The method of Clause 66, wherein, as the occlusive member self-expands, a proximal end of the occlusive member slides distally along the elongated member.

68. The method of any one of the previous Clauses, wherein delivering the embolic element occurs while the elongated member is pulled proximally.

69. The method of any one of the previous Clauses, further comprising inverting the occlusive member at a pre-determined longitude defined by a bending region.

70. The method of any one of the preceding Clauses, wherein the occlusive member is a mesh.

71. The method of any one of the preceding Clauses, wherein the occlusive member is a braid.

72. The method of any one of the preceding Clauses, wherein the occlusive member is a dual-layered braid.

73. The method of any one of the preceding Clauses, wherein the occlusive member has a globular or generally spherical shape in the first expanded state.

74. The method of any one of the preceding Clauses, wherein the occlusive member is cup or bowl-shaped in the second expanded state.

75. The method of any one of the preceding Clauses, wherein the second shape is a predetermined three-dimensional shape.

76. The method of any one of the preceding Clauses, wherein the occlusive member forms a multi-layer braid at the neck of the aneurysm in the second expanded state.

77. The method of any one of the previous Clauses, wherein the occlusive member comprises a plurality of braided filaments that assume a pre-set, three-dimensional shape in the expanded state.

78. The method of any one of the previous Clauses, wherein the occlusive member comprises a recessed portion at its distal portion.

79. The method of Clause 78, wherein an opening of the elongated member is adjacent the recessed portion such that the embolic element is delivered within the recessed portion.

80. A method for treating an aneurysm, the method comprising:
  positioning a distal end of an elongated shaft at or near an aneurysm cavity, the distal end of the shaft containing an occlusive member detachably coupled to an elongated member slidably disposed within the elongated shaft, wherein a distal end of the occlusive member is coupled to a distal end of the elongated member and a proximal end of the occlusive member is slidable over the elongated member;
  pushing the elongated member distally from a distal opening in the elongated shaft to pull a distal end of the occlusive member distally through the distal opening to expel the occlusive member from the shaft and allow the occlusive member to self-expand to a first expanded state; and
  while the occlusive member is in the first expanded state, pulling the elongated member proximally to bring a distal wall of the occlusive member towards a proximal wall of the occlusive member such that the occlusive member forms a second expanded state in which the occlusive member is collapsed on itself.

81. The method of Clause 80, further comprising delivering an embolic element through the elongated member to a position between the occlusive member and the aneurysm wall.

82. A system comprising:
  an elongate shaft defining a lumen;
  an elongate member slidably disposed within the lumen of the elongate shaft, the elongate member having a proximal end region and a distal end region, wherein the distal end region is configured to be intravascularly position at or within an aneurysm cavity;
  an occlusive member constrained within the lumen of the shaft, the occlusive member including a proximal end portion having an opening and a distal end portion detachably coupled to the distal end region of the elongate member, wherein the elongate member extends through the opening such that the
  wherein pushing the elongate member from a distal opening in the elongate shaft pulls the occlusive member distally through the distal opening to expel the occlusive member from the shaft and allow the occlusive member to expand to an expanded state.

83. The system of Clause 82, further comprising an embolic element configured to be delivered to the aneurysm cavity through the elongate member while the elongate member is coupled to the distal end portion of the occlusive member.

84. The system of Clause 83, wherein the embolic element is a liquid embolic, one or more embolic coils, or both.

85. The system of any one of Clauses 82 to 84, wherein a portion of the occlusive member surrounding the elongate member at the opening is configured to slide relative to the elongate member as the occlusive member self-expands.

86. The system of any one of Clauses 82 to 85, wherein the occlusive member comprises one or more preferential bending regions about all or a portion of the circumference of the occlusive member.

87. The system of Clause 86, wherein all or a portion of the one or more preferential bending regions comprise a radiopaque material.

88. The system of any one of Clauses 82 to 87, wherein the expanded state is a first expanded state and the occlusive member has a first shape in the first expanded state, and wherein, when the occlusive member is in the first expanded state in the aneurysm cavity and coupled to the elongate member, proximal movement of the elongate member collapses a distal wall of the occlusive member towards a proximal wall of the occlusive member, thereby transforming the occlusive member into a second expanded state in which the occlusive member has a shape different than the first shape.

89. A method for treating an aneurysm, the method comprising:
  positioning a distal end of an elongate shaft at or near an aneurysm cavity, the distal end of the shaft containing an occlusive member detachably coupled to an elongated member slidably disposed within the elongated shaft, wherein a distal end of the occlusive member is coupled to a distal end of the elongate member and a proximal end of the occlusive member is slidable over the elongate member;
  pushing the elongate member distally from a distal opening in the elongate shaft to pull a distal end of the occlusive member distally through the distal opening to expel the occlusive member from the shaft and allow the occlusive member to self-expand to a first expanded state;
  while the occlusive member is in the first expanded state, pulling the elongate member proximally to bring a distal wall of the occlusive member towards a proximal wall of the occlusive member such that the occlusive member forms a second expanded state in which at least a portion of the occlusive member is inverted; and
  delivering an embolic element through the elongate member to a position between the occlusive member and the aneurysm wall.

90. The method of Clause 89, wherein, as the occlusive member self-expands, a proximal end of the occlusive member slides distally along the elongate member.

91. The method of Clause 89 or Clause 90, wherein delivering the embolic element occurs while the elongate member is pulled proximally.

92. The method of any one of Clauses 89 to 91, further comprising inverting the occlusive member at a pre-determined longitude defined by a bending region along the occlusive member.

93. The method of any one of Clauses 89 to 92, wherein the occlusive member has a globular or generally spherical shape in the first expanded state.

94. The method of any one of Clauses 89 to 93, wherein the occlusive member is cup or bowl-shaped in the second expanded state.

95. The method of any one of Clauses 89 to 94, wherein the occlusive member forms a multi-layer braid at the neck of the aneurysm in the second expanded state, the multi-layer braid comprising a first layer corresponding to the distal wall of the occlusive member and a second layer corresponding to the proximal wall of the occlusive member.

96. A method for treating an aneurysm, the method comprising:
positioning a distal end portion of an elongated shaft at or near an aneurysm cavity, the distal end portion of the shaft containing an occlusive member detachably coupled to an elongated member slidably disposed within the elongated shaft, wherein a distal end region of the occlusive member is coupled to a distal end of the elongated member;
expanding the occlusive member within the aneurysm cavity;
pulling the elongate member proximally, thereby causing a first portion of the occlusive member to invert onto a second portion of the occlusive member, wherein the first and second portions meet at a circumferential fold;
pushing the elongate member distally, thereby causing the second portion to move away from the first portion and at least partially reversing the inversion of the occlusive member; and
delivering an embolic element through the elongate member to a space between a distal wall of the occlusive member and a wall of the aneurysm.

97. The method of Clause 96, further comprising delivering an embolic element through the elongated member to a position between the occlusive member and the aneurysm wall.

98. The method of Clause 96 or Clause 97, wherein pulling the elongate member proximally occurs at a first time and the method further comprises pulling the elongate member proximally at a second time after the first time and after pushing the elongate member distally, wherein pulling the elongate member proximally at the second time brings a distal wall of the occlusive member towards a proximal wall of the occlusive member such that the occlusive member forms a cup or bowl shape.

99. The method of Clause 98, wherein delivering the embolic element occurs while the elongate member is being pulled proximally at the second time.

100. The method of any one of Clauses 96 to 99, wherein, as the occlusive member expands, a proximal end region of the occlusive member slides distally relative to the elongate member.

101. The method of any one of Clauses 96 to 100, further comprising detaching the elongate member from the distal end region of the occlusive member and withdrawing the elongate member from the body.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

Methods for treating intracranial aneurysms in accordance with at least some embodiments of the present technology include positioning an expandable occlusive member within the aneurysm and introducing an embolic element between the occlusive member and an aneurysm wall. Introduction of the embolic element both fills space within the aneurysm cavity and deforms the occlusive member from a first expanded state to a second expanded state to fortify the occlusive member at the neck of the aneurysm. Deformation of the occlusive member from a first expanded state to a second expanded state provides the additional advantage of giving visual confirmation to the physician that the delivered amount of embolic element sufficiently fills the aneurysm cavity. In addition to providing a structural support and anchor for the embolic element, the occlusive member provides a scaffold for tissue remodeling and diverts blood flow from the aneurysm. Moreover, the embolic element exerts a substantially uniform pressure on the occlusive member towards the neck of the aneurysm, thereby pressing the portions of the occlusive member positioned adjacent the neck against the inner surface of the aneurysm wall such that the occlusive member forms a complete and stable seal at the neck.

Specific details of systems, devices, and methods for treating intracranial aneurysms in accordance with embodiments of the present technology are described herein with reference to FIGS. 1A-7J. Although these systems, devices, and methods may be described herein primarily or entirely in the context of treating saccular intracranial aneurysms, other contexts are within the scope of the present technology. For example, suitable features of described systems, devices, and methods for treating saccular intracranial aneurysms can be implemented in the context of treating non-saccular intracranial aneurysms, abdominal aortic aneurysms, thoracic aortic aneurysms, renal artery aneurysms, arteriovenous malformations, tumors (e.g. via occlusion of vessel(s) feeding a tumor), perivascular leaks, varicose veins (e.g. via occlusion of one or more truncal veins such as the great saphenous vein), hemorrhoids, and sealing endoleaks adjacent to artificial heart valves, covered stents, and abdominal aortic aneurysm devices among other examples. Furthermore, it should be understood, in general, that other systems, devices, and methods in addition to those disclosed herein are within the scope of the present disclosure. For example, systems, devices, and methods in accordance with embodiments of the present technology can have different and/or additional configurations, components, procedures, etc. than those disclosed herein. Moreover, systems, devices, and methods in accordance with embodiments of the present disclosure can be without one or more of the configurations, components, procedures, etc. disclosed herein without deviating from the present technology.

I. Overview of Systems of the Present Technology

Figure 1A:
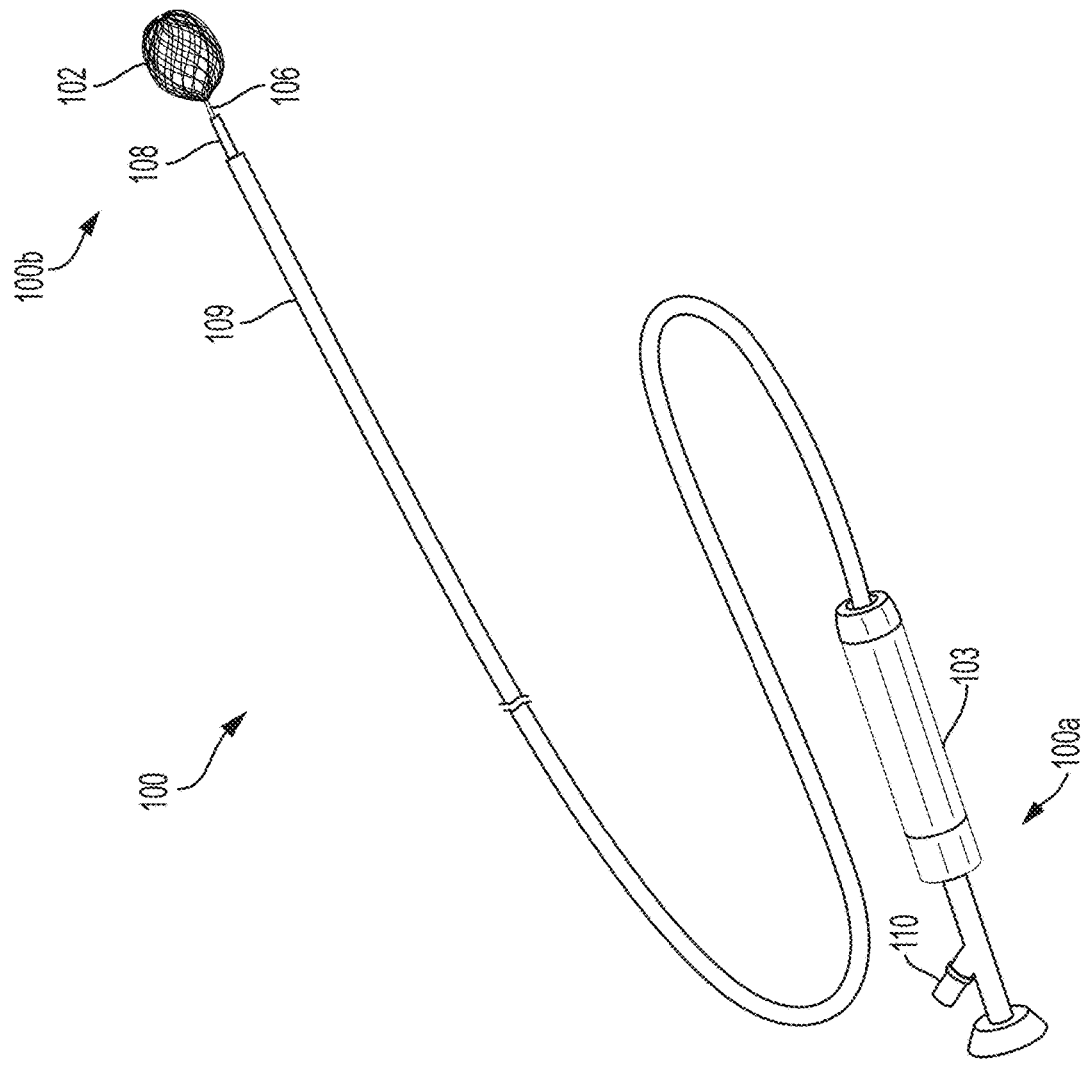
FIG. 1A shows a perspective view of a system for treating an aneurysm in accordance with the present technology.

FIG. 1A illustrates a view of a system 10 for treating intracranial aneurysms according to one or more embodiments of the present technology. As shown in FIG. 1A, the system 10 comprises a treatment system 100 and an embolic kit 200 for use with one or more components of the treatment system 100. The treatment system 100 may comprise an occlusive member 102 (shown in an expanded state) detachably coupled to a delivery system, and the delivery system may be configured to intravascularly position the occlusive member 102 within an aneurysm. The embolic kit 200 may comprise one or more substances or devices that alone or in combination form an embolic element that is configured to co-occupy the internal volume of the aneurysm with the occlusive member 102. In some embodiments, the treatment system 100 may be configured to deliver the embolic element (and/or one or more precursors thereof) to the aneurysm. Additionally or alternatively, the system 10 may include a separate delivery system (not shown) for delivering the embolic element (and/or one or more precursors thereof) to the aneurysm cavity.

As shown in FIG. 1A, the treatment system 100 has a proximal portion 100a configured to be extracorporeally positioned during treatment and a distal portion 100b configured to be intravascularly positioned within a blood vessel (such as an intracranial blood vessel) at a treatment site at or proximate an aneurysm. The treatment system 100 may include a handle 103 at the proximal portion 100a, the occlusive member 102 at the distal portion 100b, and a plurality of elongated shafts or members extending between the proximal and distal portions 100a and 100b. In some embodiments, such as that shown in FIG. 1A, the treatment system 100 may include a first elongated shaft 109 (such as a guide catheter or balloon guide catheter), a second elongated shaft 108 (such as a microcatheter) configured to be slidably disposed within a lumen of the first elongated shaft 109, and an elongated member 106 configured to be slidably disposed within a lumen of the second elongated shaft 108. In some embodiments, the treatment system 100 does not include the first elongated shaft 109 and only includes the second elongated shaft 108.

Figure 1B:
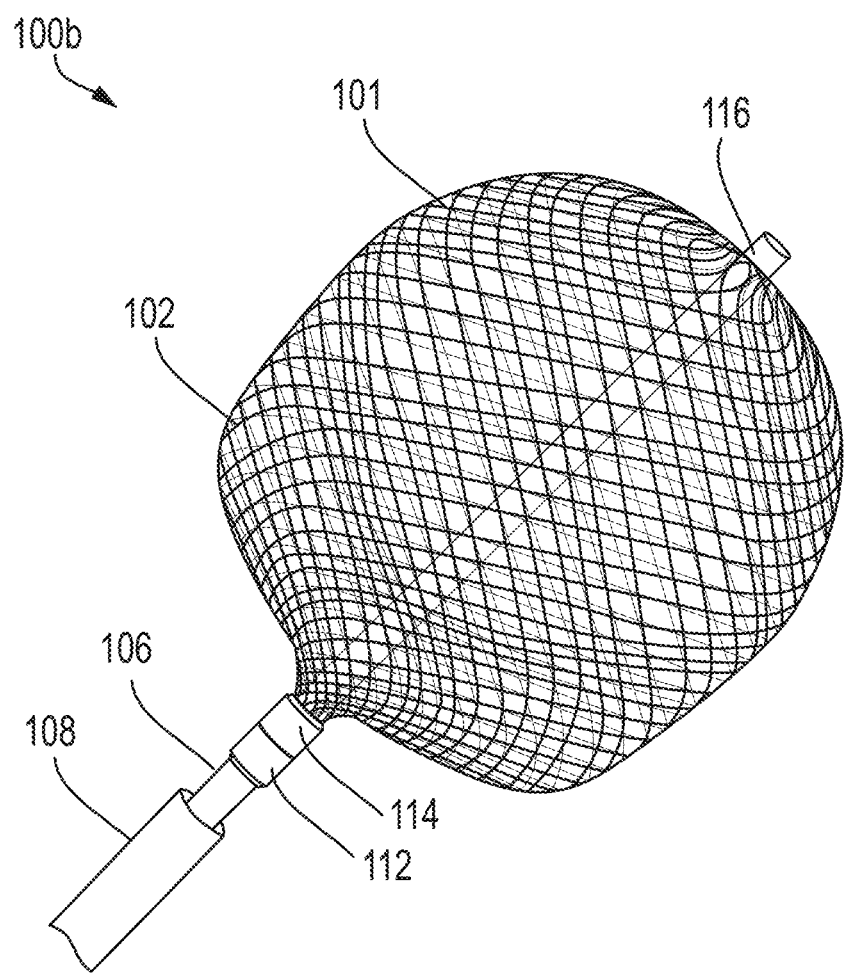
FIG. 1B shows an enlarged view of a distal portion of the treatment system of FIG. 1A in accordance with the present technology.

FIG. 1B is an enlarged view of the distal portion 100b of the treatment system 100. Referring to FIGS. 1A and 1B together, the occlusive member 102 may be detachably coupled to a distal end of the elongated member 106. For example, the elongated member 106 may include a first coupler 112 at its distal end, and the occlusive member 102 may include a second coupler 114 configured to detachably couple with the first coupler 112. The treatment system 100 may further comprise a conduit 116 extending from the handle 103 (for example, via port 110) distally to the distal portion 100b of the treatment system 100. The conduit 116 is configured to deliver the embolic element (and/or one or more precursors thereof) through one or more components of the delivery system (e.g., the first or second elongated shafts 109, 108, the elongated member 106, etc.) to a position at the exterior of the occlusive member 102. As such, the embolic element may be positioned between the occlusive member 102 and an inner wall of the aneurysm cavity, as described in greater detail below.

According to some embodiments, the second elongated shaft 108 is generally constructed to track over a conventional guidewire in the cervical anatomy and into the cerebral vessels associated with the brain and may also be chosen according to several standard designs that are generally available. Accordingly, the second elongated shaft 108 can have a length that is at least 125 cm long, and more particularly may be between about 125 cm and about 175 cm long. In some embodiments, the second elongated shaft 108 may have an inner diameter of about 0.015 inches (0.0381 cm), 0.017 inches (0.043 cm), about 0.021 inches (0.053 cm), or about 0.027 inches (0.069 cm). Other designs and dimensions are contemplated.

The elongated member 106 can be movable within the first and/or second elongated shafts 109, 108 to position the occlusive member 102 at a desired location. The elongated member 106 can be sufficiently flexible to allow manipulation, e.g., advancement and/or retraction, of the occlusive member 102 through tortuous passages. Tortuous passages can include, for example, catheter lumens, microcatheter lumens, blood vessels, urinary tracts, biliary tracts, and airways. The elongated member 106 can be formed of any material and in any dimensions suitable for the task(s) for which the system is to be employed. In some embodiments, the elongated member 106 can comprise a solid metal wire. In some embodiments, the elongated member 106 may comprise any other suitable form of shaft such as an elongated tubular shaft.

In some embodiments, the elongated member 106 can comprise stainless steel, nitinol, cobalt chrome, or other metal or alloy. In some embodiments, the elongated member 106 can be surrounded over some or all of its length by a coating, such as, for example, polytetrafluoroethylene. The elongated member 106 may have a diameter that is generally constant along its length, or the elongated member 106 may have a diameter that tapers radially inwardly, along at least a portion of its length, as it extends in a distal direction.

According to several embodiments, the conduit 116 may be a catheter or elongated shaft that is delivered separately from the second elongated shaft 108.

A. Selected Examples of Occlusive Members

Figure 1C:
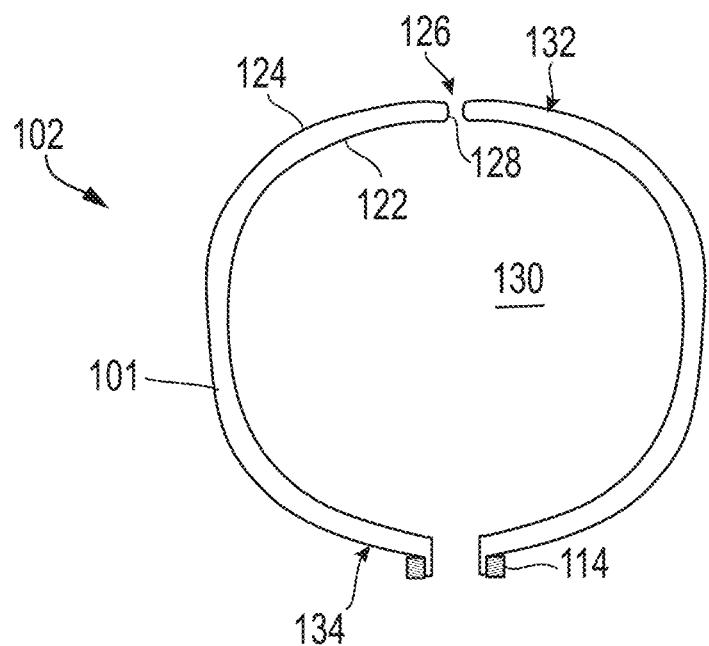
FIGS. 1C and 1D are sectioned views of occlusive members in an expanded state in accordance with the present technology.

FIG. 1C is a sectioned view of the occlusive member 102, shown in an expanded state and detached from the treatment system 100. Referring to FIGS. 1B and 1C, the occlusive member 102 may comprise an expandable element having a low-profile or constrained state while positioned within a catheter (such as the second elongated shaft 108) for delivery to the aneurysm and an expanded state in which the expandable element is configured to be positioned within an aneurysm (such as a cerebral aneurysm).

According to some embodiments, the occlusive member 102 may comprise a mesh 101 formed of a plurality of braided filaments that have been heat-set to assume a predetermined shape enclosing an interior volume 130 when the mesh 101 is in an expanded, unconstrained state. Example shapes include a globular shape, such as a sphere, a prolate spheroid, an oblate spheroid, and others. As depicted in FIG. 1C, the mesh 101 may have inner and outer layers 122, 124 that have proximal ends fixed relative to one another at the second coupler 114 and meet distally at a distal fold 128 surrounding an aperture 126. While the inner and outer layers 122, 124 are depicted spaced apart from one another along their lengths, the inner and outer layers 122, 124 may be in contact with one another along all or a portion of their lengths. For example, the inner layer 122 may press radially outwardly against the outer layer 124. In some embodiments, the occlusive member 102 may be formed of a single layer or mesh or braid.

In some embodiments, the inner and outer layers 122, 124 have their distal ends fixed relative to one another at a distal coupler and meet proximally at a proximal fold surrounding an aperture. In any case, in some embodiments the conduit 116 may be configured to be slidably positioned through some or all of the second coupler 114, the interior volume 130 of the expanded mesh 101, and the opening 126.

The inner and outer layers 122 and 124 may conform to one another at the distal portion (for example as shown in FIG. 1C) to form a curved distal surface. For example, at least at the distal portion of the occlusive member 102, the inner and outer layers 122 and 124 may extend distally and radially inwardly, towards the aperture 126. In some embodiments, the outer and/or inner layers 122 and 124 extend distally and radially outwardly from the second coupler 114, then extend distally and radially inwardly up to a distal terminus of the occlusive member 102 (e.g., the fold 128). The occlusive member 102 and/or layers thereof may be curved along its entire length, or may have one or more generally straight portions. In some embodiments, the curved surface transitions to a flat or substantially flat, distal-most surface that surrounds the aperture 126. In some embodiments, the curved surface transitions to a distal-most surface that surrounds the aperture 126 and has a radius of curvature that is greater than the average radius of curvature of the rest of the occlusive member 102. Having a flat or substantially flat distal surface, or a distal surface with a radius of curvature that is greater than the average radius of curvature of the rest of the occlusive member 102, may be beneficial for delivering the embolic element 230 in that it creates a small gap between the distal surface of the occlusive member 102 and the dome of the aneurysm A (see, for example, FIG. 3B). In some embodiments, the surface of the occlusive member 102 surrounding the aperture 126 is curved and/or has generally the same radius of curvature as the remainder of the occlusive member 102.

Figure 1D:
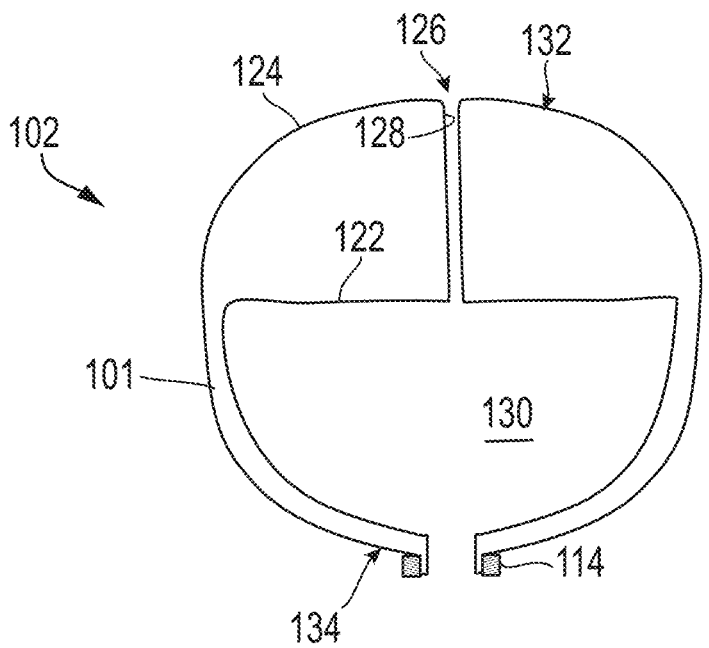
Figure 2:
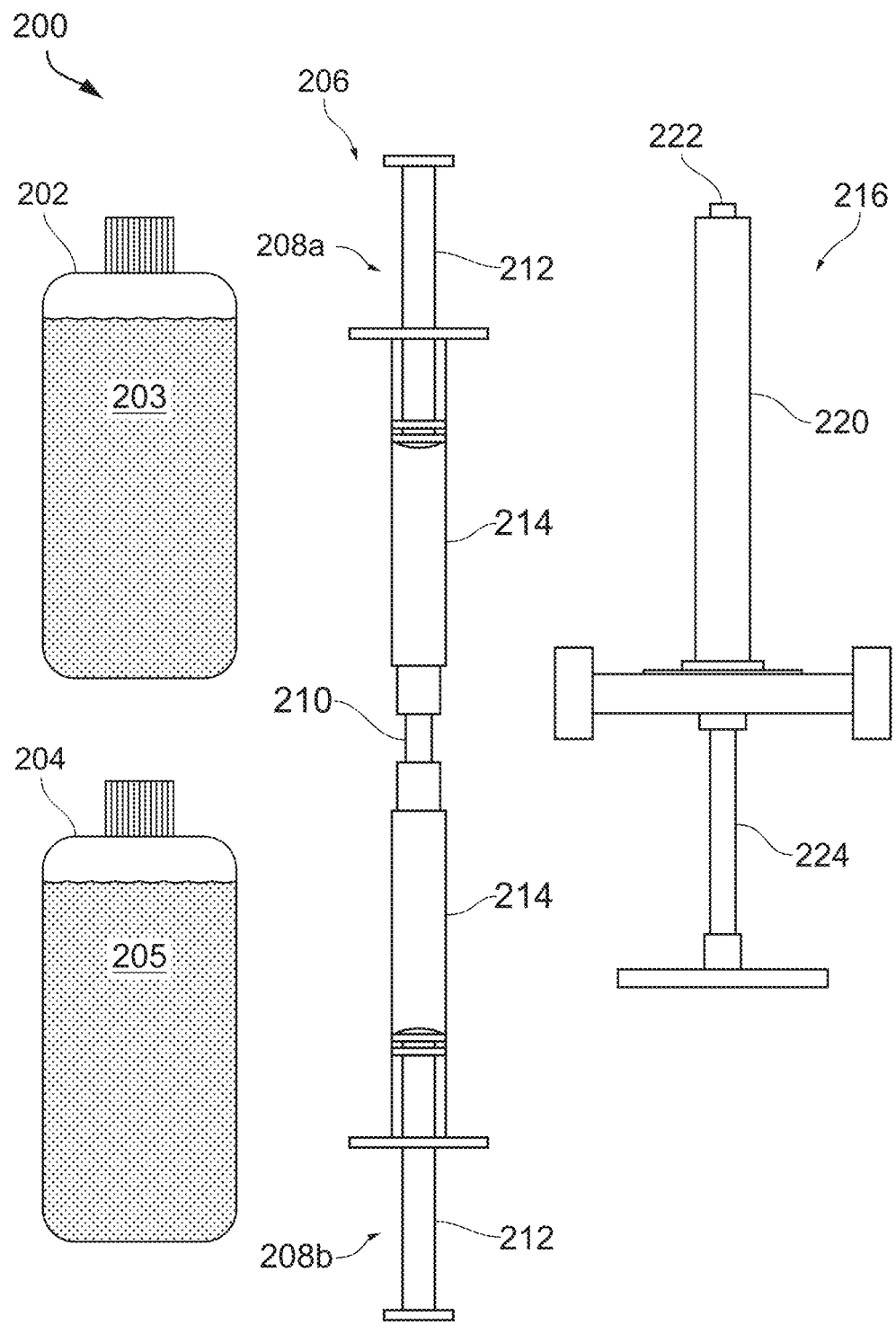
FIG. 2 shows an embolic kit according to the present technology.

In any case, the inner layer 124 may have a shape that substantially conforms to the shape of the outer layer 124, or the inner and outer layers 122, 124 may have different shapes. For example, as shown in FIG. 1D, the inner layer 122 may have a diameter or cross-sectional dimension that is less than the outer layer 124. Such a configuration may be beneficial in that the embolic element 230 experiences less resistance, at least initially, when pushing the distal wall of the occlusion member 102 downwardly towards the neck (as described in greater detail below).

In any case, both the proximal portion and the distal portion of the mesh 101 can form generally closed surfaces. However, unlike at the proximal portion of the mesh 101, the portion of the filaments at or near the fold 128 at the distal portion of the mesh 101 can move relative to one another. As such, the distal portion of the mesh 101 has both the properties of a closed end and also some properties of an open end (like a traditional stent), such as some freedom of movement of the distal-most portions of the filaments and an opening through which the conduit 116, a guidewire, guidetube, or other elongated member may pass through.

In some embodiments, each of the plurality of filaments have a first end positioned at the proximal portion of the mesh 101 and a second end also positioned at the proximal portion of the mesh 101. Each of the filaments may extend from its corresponding first end distally along the body of the mesh 101 to the fold 128, invert, then extend proximally along the mesh body to its corresponding second end at the proximal portion of the mesh 101. As such, each of the plurality of filaments have a first length that forms the inner layer 122 of the mesh 101, a second length that forms the outer layer 124 of the mesh 101, and both first and second ends fixed at the proximal portion of the mesh 101. In some embodiments, the occlusive member 102 may comprise a mesh formed of a single layer, or a mesh formed of three or more layers.

In some embodiments, the distal end surface of the mesh 101 is completely closed (i.e., does not include an aperture). In some embodiments the filaments are fixed relative to the at both the proximal and distal ends of the occlusive member 102.

The mesh 101 may be formed of metal wires, polymer wires, or both, and the wires may have shape memory and/or superelastic properties. The mesh 101 may be formed of 24, 32, 36, 48, 64, 72, 96, 128, or 144 filaments. The mesh 101 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh 101 may have the same diameter. For example, in some embodiments, all of the filaments have a diameter of about 0.001 inches. In some embodiments, some of the filaments may have different cross-sectional diameters. For example, some of the filaments may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling-out the braid matrix density.

The occlusive member 102 can have different shapes and sizes in an expanded, unconstrained state. For example, the occlusive member 102 may have a bullet shape, a barrel-shape, an egg shape, a dreidel shape, a bowl shape, a disc shape, a cylindrical or substantially cylindrical shape, a barrel shape, a chalice shape, etc.

B. Selected Examples of Embolic Kits

The embolic kit 200 may include one or more precursors for creation of a liquid embolic. For example, the embolic kit 200 may include a first container 202 containing a first precursor material 203 (shown schematically), a second container 204 containing a second precursor material 205 (also shown schematically), and a mixing device 206 suitable for mixing the first and second precursor materials 203, 205. The mixing device 206 can include mixing syringes 208 (individually identified as mixing syringes 208a, 208b) and a coupler 210 extending between respective exit ports (not shown) of the mixing syringes 208. The mixing syringes 208a, 208b each include a plunger 212 and a barrel 214 in which the plunger 212 is slidably received.

The embolic kit 200 can further include an injection syringe 216 configured to receive a mixture of the first and second precursor materials 203, 205 and deliver the mixture to a proximal portion 100b of the treatment assembly 100. The injection syringe 216 can include a barrel 220, an exit port 222 at one end of the barrel 220, and a plunger 224 slidably received within the barrel 220 via an opposite end of the barrel 220. The handle 103 of the treatment system 100 may have a coupler configured to form a secure fluidic connection between the lumen and the exit port 222 of the injection syringe 216.

The first and second precursor materials 203, 205 can include a biopolymer and a chemical crosslinking agent, respectively. The chemical crosslinking agent can be selected to form covalent crosslinks between chains of the biopolymer. In some embodiments, the biopolymer of the first precursor material 203 includes chitosan or a derivative or analog thereof, and the chemical crosslinking agent of the second precursor material 205 includes genipin or a derivative or analog thereof. Other suitable crosslinking agents for use with chitosan include glutaraldehyde, functionalized polyethylene glycol, and derivatives and analogs thereof. In other embodiments, the biopolymer of the first precursor material 203 can include collagen or a derivative or analog thereof, and the chemical crosslinking agent of the second precursor material 205 can include hexamethylene diisocyanate or a derivative or analog thereof. Alternatively or in addition, genipin or a derivative or analog thereof can be used as a chemical crosslinking agent for a collagen-based biopolymer. In still other embodiments, the biopolymer of the first precursor material 203 and the chemical crosslinking agent of the second precursor material 205 can include other suitable compounds alone or in combination.

Mixing the biopolymer of the first precursor material 203 and the chemical crosslinking agent of the second precursor material 205 can initiate chemical crosslinking of the biopolymer. After the first and second precursor materials 203, 205 are mixed, chemical crosslinking of the biopolymer occurs for enough time to allow the resulting embolic element 230 be delivered to the aneurysm before becoming too viscous to move through the lumen of the conduit 116. In addition, the period of time during which chemical crosslinking of the biopolymer occurs can be short enough to reach a target deployed viscosity within a reasonable time (e.g., in the range of 10-60 minutes; or at most 40 minutes, 30 minutes, 20 minutes, or 10 minutes) after delivery. The target deployed viscosity can be high enough to cause an agglomeration of the embolic element 230 to remain within the internal volume of the aneurysm without reinforcing the neck.

In at least some cases, the biopolymer has a non-zero degree of chemical crosslinking within the first precursor material 203 before mixing with the chemical crosslinking agent. This can be useful, for example, to customize the curing window for the embolic element 230 so that it corresponds well with an expected amount of time needed to deliver the material to the aneurysm. The degree of chemical crosslinking of the biopolymer within the first precursor material 203 before mixing with the chemical crosslinking agent, the ratio of the biopolymer to the chemical crosslinking agent, and/or one or more other variables can be selected to cause the embolic element 230 to have a viscosity suitable for delivery to the aneurysm via the lumen of the conduit 116 for a suitable period of time (e.g., a period within a range from 10 minutes to 40 minutes) after mixing of the first and second precursor materials 203, 205. In at least some cases, the first and second precursor materials 203, 205 are mixed in proportions that cause a weight ratio of the biopolymer to the chemical crosslinking agent in the resulting embolic element 230 to be within a range from 10:1 to 100:1, such as from 10:1 to 30:1, or from 15:1 to 50:1, or from 15:1 to 25:1. In a particular example, the first and second precursor materials 203, 205 are mixed in proportions that cause a weight ratio of the biopolymer to the chemical crosslinking agent in the resulting embolic element 230 to be 30:1.

Use of a biopolymer instead of an artificial polymer in the first precursor material 203 may be advantageous because biopolymers tend to be more readily bioabsorbed than artificial polymers and/or for other reasons. Furthermore, use of a chemical crosslinking agent instead of a physical crosslinking agent (i.e., a crosslinking agent that forms noncovalent crosslinks between chains of the biopolymer) in the second precursor material 205 may be advantageous because chemically crosslinked polymers tend to be more cohesive than physically crosslinked polymers and/or for other reasons. In the context of forming a tissue scaffold within an aneurysm, high cohesiveness of the embolic element 230 may be more important than it is in other contexts to secure the cured embolic element 230 within the aneurysm 302. For example, high cohesiveness of the embolic element 230 may reduce or eliminate the possibility of a piece of the embolic element 230 breaking free and entering a patient's intracerebral blood stream during delivery.

The first and second precursor materials 203, 205 may include other components and/or the system 200 may include other precursor materials intended for mixing with the first and second precursor materials 203, 205. For example, the first, second, and/or another precursor material may include a physical crosslinking agent. The presence of a physical crosslinking agent may be useful to form physical crosslinks that complement chemical crosslinks from the chemical crosslinking agent. The combination of chemical and physical crosslinks may enhance the cohesiveness of the embolic element 230. Suitable physical crosslinking agents for use with chitosan-based biopolymers include β glycerophosphate, mannitol, glucose, and derivatives and analogs thereof. In these and other cases, the embolic element 230 may include multiple chemical crosslinking agents and/or multiple physical crosslinking agents.

A contrast agent is another component that may be added to the precursor materials. The presence of a contrast agent within the embolic element 230 can be useful to visualize delivery of the embolic element 230 using fluoroscopy. One problem with using conventional platinum coils in intracranial aneurysms is that the persistent radiopacity of the coils tends to interfere with visualizing other aspects of the treatment in follow-up imaging. For example, the presence of platinum coils within an aneurysm may make it difficult or impossible to detect by fluoroscopy the presence of blood-carried contrast agent that would otherwise indicate recanalization. In at least some embodiments of the present technology, a contrast agent within the embolic element 230 is selected to provide radiopacity that diminishes over time. For example, the contrast agent may initially be radiopaque to facilitate delivery of the embolic element 230 and then become less radiopaque to facilitate follow-up imaging. In a particular example, the first, second, and/or another precursor material includes iohexol or a derivative or analog thereof as a suitable contrast agent.

In animal studies, the liquid embolics of the present technology were shown to provide (a) complete or nearly complete volumetric filling of the aneurysm internal volume, and (b) complete or nearly complete coverage of the aneurysm neck with new endothelial tissue. These features, among others, are expected to result in a lower recanalization rate than that of platinum coil treatments and faster aneurysm occlusion than that of flow diverters. Furthermore, the injectable scaffold material is expected to be bioabsorbed and thereby reduced in volume over time. Thus, unlike platinum coils, the injectable scaffold is expected to have little or no long-term mass effect. Furthermore, the injectable scaffold material can be configured to have diminishing radiopacity; therefore, when so configured it will not interfere future CT and MRI imaging and procedures. Embodiments of the present technology can have these and/or other features and advantages relative to conventional counterparts whether or not such features and advantages are described herein.

In some embodiments, the embolic kit 200 and/or embolic element 230 may be any embolic or occlusive device, such as one or more embolic coils, polymer hydrogel(s), polymer fibers, mesh devices, or combinations thereof. The embolic kit 200 may include one or more precursors that, once mixed together, form the embolic element 230 that remains within the aneurysm. In some embodiments, the embolic kit 200 may include the embolic element pre-mixed.

II Selected Methods for Treating Aneurysms

FIGS. 3A-3G depict an example method for treating an aneurysm A with the systems 10 of the present technology. To begin, a physician may intravascularly advance the second elongated shaft 108 towards an intracranial aneurysm (or other treatment location such as any of those described herein) with the occlusive member 102 in a low-profile state. A distal portion of the second elongated shaft 108 may be advanced through a neck N of the aneurysm A to locate a distal opening of the second elongated shaft 108 within an interior cavity of the aneurysm A. The elongated member 106 may be advanced distally relative to the second elongated shaft 108 to push the occlusive member 102 through the opening at the distal end of the second elongated shaft 108, thereby releasing the occlusive member 102 from the shaft 108 and allowing the occlusive member 102 to self-expand into a first expanded state.

Figure 3A:
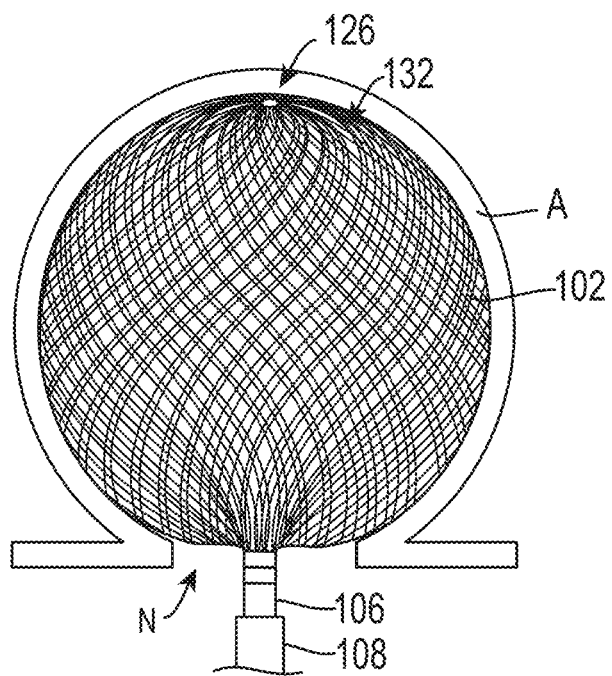
FIGS. 3A-3G depict an example method of treating an aneurysm with the treatment systems of the present technology.
Figure 3B:
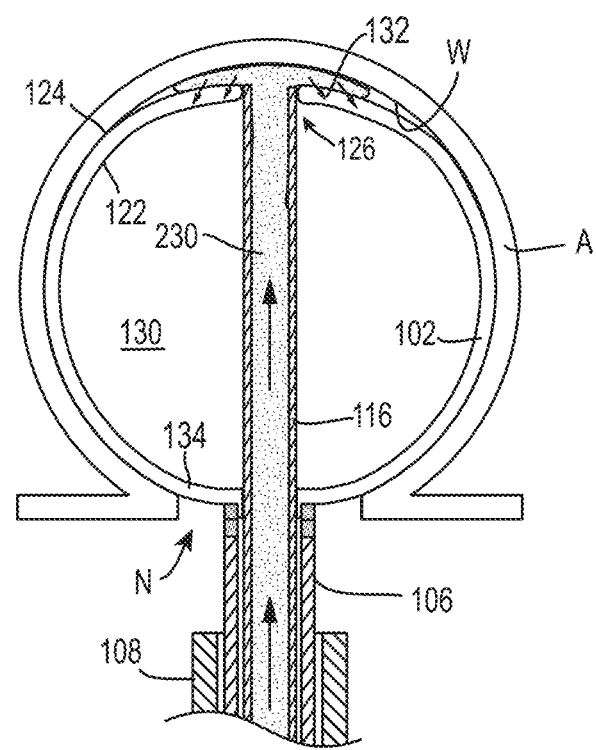

FIG. 3A shows the occlusive member 102 in a first expanded state, positioned in an aneurysm cavity and still coupled to the elongated member 106. As shown in FIG. 3A, in the first expanded state, the occlusive member 102 may assume a predetermined shape that encloses an internal volume 130 (see FIG. 1C). In this first expanded state, the occlusive member 102 may generally conform to the shape of the aneurysm A. As illustrated in FIG. 3B with the occlusive member 102 and delivery system shown in cross-section, the conduit 116 may be advanced through the internal volume 130 of the occlusive member 102 such that a distal opening of the conduit 116 is at or distal to the aperture 126 at the distal portion of the occlusive member 102. The embolic element 230 may be delivered through the conduit 116 to a space between the occlusive member 102 and an inner surface of the aneurysm wall W.

In some embodiments, the method includes mixing the first and second precursor materials 203, 205 (FIG. 2) to form the embolic element 230. Mixing of the first and second precursor materials 203, 205 may occur prior to introducing the embolic element 230 to the treatment system 100 and/or during delivery of the embolic element through the conduit 116 to the aneurysm. In a particular example, the first precursor material 203 is loaded into one of the barrels 214, the second precursor materials 205 is loaded into the other barrel 214, and the mixing syringes 208 are coupled via the coupler 210. To mix the first and second precursor materials 203, 205, the plungers 212 are alternately depressed, thereby causing the first and second precursor materials 203, 205 to move repeatedly from one barrel 214 to the other barrel 214. After suitably mixing the precursor materials, the resulting embolic element 230 can be loaded into the barrel 220 of the injection syringe 216. The injection syringe 216 may then be coupled to a proximal end of the conduit 116 to deliver the embolic element 230 through the conduit 116 and into the aneurysm A. As the embolic element 230 passes through the lumen of the conduit 116, chemical crosslinking of the biopolymer can continue to occur.

Figure 3C:
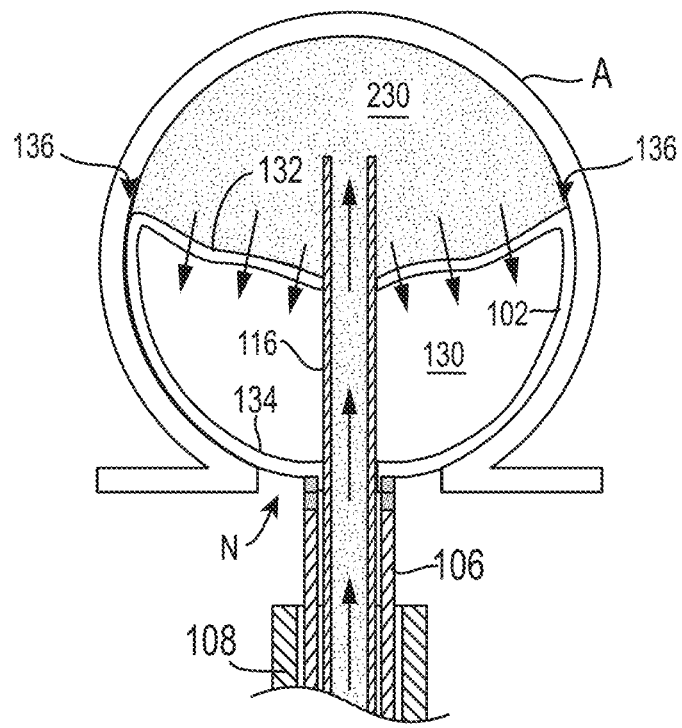
Figure 3D:
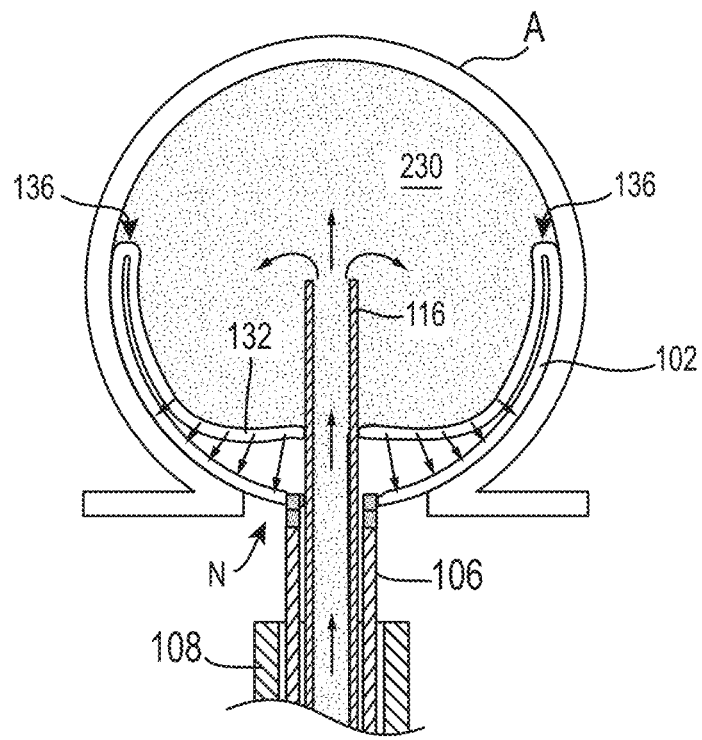

Still with reference to FIG. 3B, as the embolic element 230 is delivered between the dome of the aneurysm A and the distal portion 132 of the wall of the occlusive member 102, pressure builds between the aneurysm wall W and the occlusive member 102. As shown in the progression of FIGS. 3B-3D, when the forces on the occlusive member 102 reach a threshold level, the embolic element 230 pushes the distal wall 132 downwardly towards the neck N of the aneurysm A. The embolic element 230 exerts a substantially uniform pressure across the distal surface of the occlusive member 102 that collapses the occlusive member 102 inwardly on itself such that the rounded distal wall 132 transitions from concave towards the neck N of the aneurysm A to convex towards the neck N. The pressure and inversion of the distal portion of the wall 132 creates an annular fold 136 that defines the distal-most edge of the occlusive member 102. As the occlusive member 102 continues to invert, the position of the fold 136 moves towards the neck N, which continues until a distal-most half of the occlusive member 102 has inverted. In some embodiments, the occlusive member 102 may include one or more portions configured to preferentially flex or bend such that the occlusive member 102 folds at a desired longitude (for example, as discussed in greater detail below with respect to FIGS. 5-7J. Moreover, as the occlusive member 102 collapses, a distance between the wall at the distal portion 132 and the wall at the proximal portion decreases, and thus the internal volume 130 of the occlusive member 102 also decreases. As the occlusive member 102 collapses, the conduit 116 may be held stationary, advanced distally, and/or retracted proximally.

During and after delivery of the embolic element 230, none or substantially none of the embolic element 230 migrates through the pores of the occlusive member 102 and into the internal volume 130. Said another way, all or substantially all of the embolic element 230 remains at the exterior surface or outside of the occlusive member 102. Compression of the occlusive member with the embolic element 230 provides a real-time "leveling" or "aneurysm-filling indicator" to the physician under single plane imaging methods (such as fluoroscopy) so that the physician can confirm at what point the volume of the aneurysm is completely filled. Additional details regarding devices, systems, and methods for monitoring and/or confirming deployment are described below with reference to FIGS. 4A-5B. It is beneficial to fill as much space in the aneurysm as possible, as leaving voids within the aneurysm sac may cause delayed healing and increased risk of aneurysm recanalization and/or rupture. While the scaffolding provided by the occlusive member 102 across the neck helps thrombosis of blood in any gaps and healing at the neck, the substantial filling of the cavity prevents rupture acutely and does not rely on the neck scaffold (i.e., the occlusive member 102). Confirmation of complete or substantially complete aneurysm filling under single plane imaging cannot be provided by conventional devices.

Once delivery of the embolic element 230 is complete, the conduit 116 may be withdrawn. In some embodiments, the embolic element 230 may fill greater than 40% of the aneurysm sac volume. In some embodiments, the embolic element 230 may fill greater than 50% of the aneurysm sac volume. In some embodiments, the embolic element 230 may fill greater than 60% of the aneurysm sac volume. In some embodiments, the embolic element may fill greater than 65%, 70%, 75%, 80%, 85%, or 90% of the aneurysm sac volume.

Figure 3E:
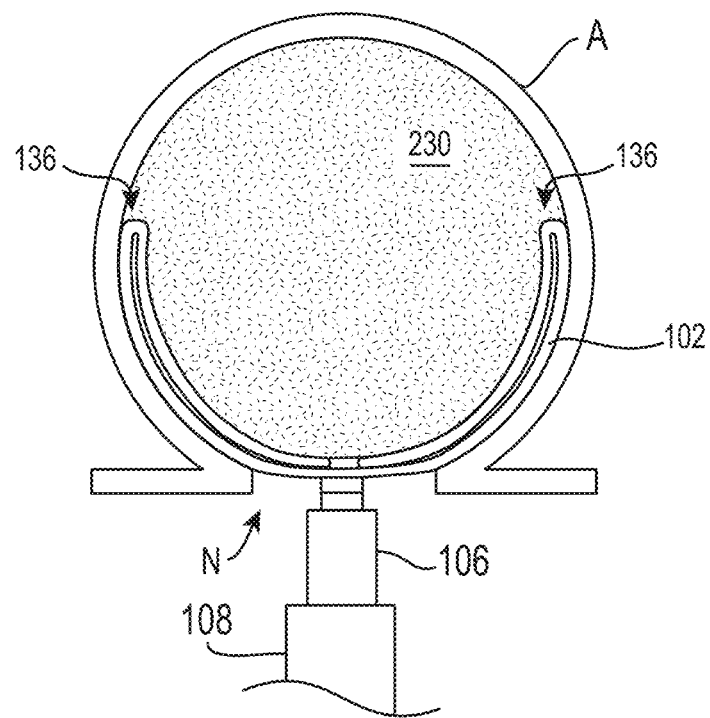
Figure 3F:
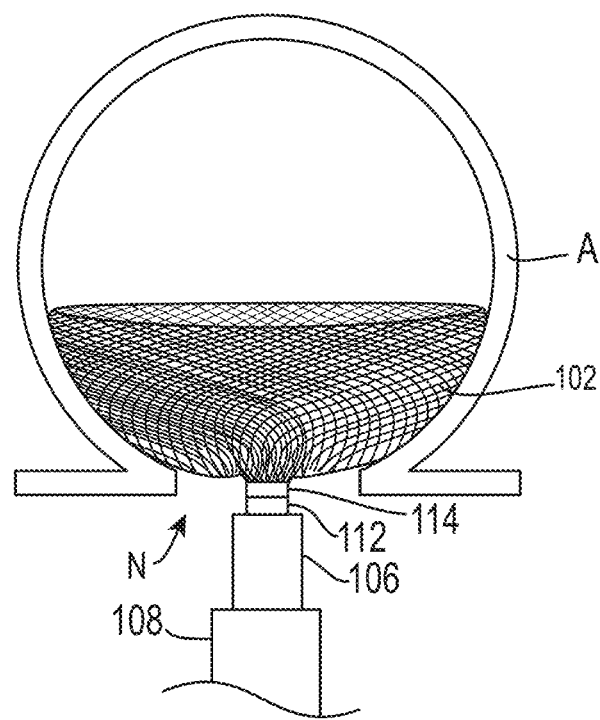

FIG. 3E shows a second expanded state of the occlusive member 102, shown in cross-section, with the embolic element 230 occupying the remaining volume of the aneurysm A. FIG. 3F shows the occlusive member 102 in full with the embolic element 230 removed so the second shape of the occlusive member 102 is visible. As shown, the embolic element 230 may be delivered until the occlusive member 102 is fully-collapsed such that the occlusive member 102 has substantially no internal volume.

In the second expanded state, the occlusive member 102 may form a bowl shape that extends across the neck of the aneurysm A. The wall of the occlusive member 102 at the distal portion may now be positioned in contact with or immediately adjacent the wall of the occlusive member 102 at the proximal portion. The distal wall 132 may be in contact with the proximal wall 134 along all or substantially all of its length. In some embodiments, the distal wall 132 may be in contact with the proximal wall 134 along only a portion of its length, while the remainder of the length of the distal wall 132 is in close proximity—but not in contact with—the proximal wall 134.

Collapse of the occlusive member 102 onto itself, towards the neck N of the aneurysm, may be especially beneficial as it doubles the number of layers across the neck and thus increases occlusion at the neck N. For example, the distal wall 132 collapsing or inverting onto the proximal wall 134 may decrease the porosity of the occlusive member 102 at the neck N. In those embodiments where the occlusive member 102 is a mesh or braided device such that the distal wall 132 has a first porosity and the proximal wall 134 has a second porosity, deformation of the distal wall 132 onto or into close proximity within the proximal wall 134 decreases the effective porosity of the occlusive member 102 over the neck N. The resulting multi-layer structure thus has a lower porosity than the individual first and second porosities. Moreover, the embolic element 230 along the distal wall 132 provides additional occlusion. In some embodiments, the embolic element 230 completely or substantially completely occludes the pores of the adjacent layer or wall of the occlusion member 102 such that blood cannot flow past the embolic element 230 into the aneurysm cavity. It is desirable to occlude as much of the aneurysm as possible, as leaving voids of gaps can allow blood to flow in and/or pool, which may continue to stretch out the walls of aneurysm A. Dilation of the aneurysm A can lead to recanalization and/or herniation of the occlusive member 102 and/or embolic element 230 into the parent vessel and/or may cause the aneurysm A to rupture. Both conditions can be fatal to the patient.

In those embodiments where the wall of the occlusive member 102 comprises an inner and outer layer, the deformed or second shape of the occlusive member 102 forms four layers over the neck N of the aneurysm A In those embodiments where the wall of the occlusive member 102 comprises a single layer, the deformed or second shape of the occlusive member 102 forms two layers over the neck N of the aneurysm A As previously mentioned, the neck coverage provided by the doubled layers provides additional surface area for endothelial cell growth, decreases the porosity of the occlusive member 102 at the neck N (as compared to two layers or one layer), and prevents herniation of the embolic element 230 into the parent vessel. During and after delivery, the embolic element 230 exerts a substantially uniform pressure on the occlusive member 102 towards the neck N of the aneurysm A, thereby pressing the portions of the occlusive member 102 positioned adjacent the neck against the inner surface of the aneurysm wall such that the occlusive member 102 forms a complete and stable seal at the neck N.

Figure 3G:
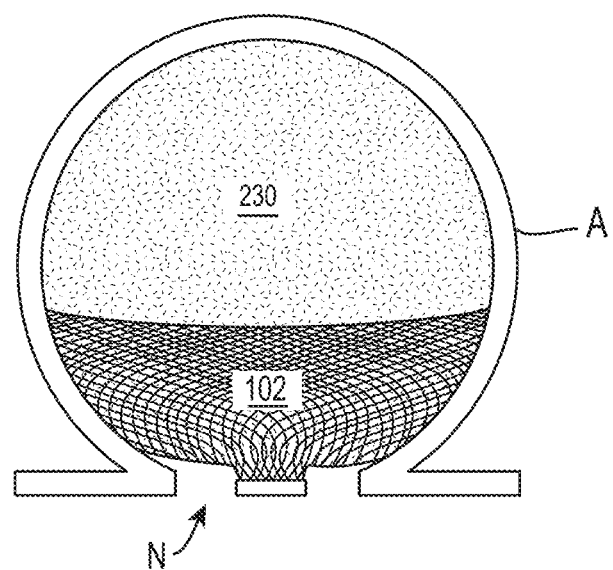

As shown in FIG. 3G, the first coupler 112 may be detached from the second coupler 114 and the elongated member 106 and second elongated shaft 108 may be withdrawn, thereby leaving the occlusive member 102 and embolic element 230 implanted within the aneurysm A.

Over time natural vascular remodeling mechanisms and/or bioabsorption of the embolic element 230 may lead to formation of a thrombus and/or conversion of entrapped thrombus to fibrous tissue within the internal volume of the aneurysm A. These mechanisms also may lead to cell death at a wall of the aneurysm and growth of new endothelial cells between and over the filaments or struts of the occlusive device 102. Eventually, the thrombus and the cells at the wall of the aneurysm may fully degrade, leaving behind a successfully remodeled region of the blood vessel.

In some embodiments, contrast agent can be delivered during advancement of the occlusive member 102 and/or embolic element 230 in the vasculature, deployment of the occlusive member 102 and/or embolic element 230 at the aneurysm A, and/or after deployment of the occlusive member 102 and/or embolic element 230 prior to initiation of withdrawal of the delivery system. The contrast agent can be delivered through the second elongated shaft 108, the conduit 116, or through another catheter or device commonly used to delivery contrast agent. The aneurysm (and devices therein) may be imaged before, during, and/or after injection of the contrast agent, and the images may be compared to confirm a degree of occlusion of the aneurysm.

According to some aspects of the technology, the system 10 may comprise separate first and second elongated shafts (e.g., microcatheters) (not shown), the first dedicated to delivery of the embolic element, and the second dedicated to the delivery of the occlusive member. In example methods of treating an aneurysm, the first elongated shaft may be intravascularly advanced to the aneurysm and through the neck such that that a distal tip of the first elongated shaft is positioned within the aneurysm cavity. In some embodiments, the first elongated shaft may be positioned within the aneurysm cavity such that the distal tip of the shaft is near the dome of the aneurysm.

The second elongated shaft containing the occlusive member (such as occlusive member 102) may be intravascularly advanced to the aneurysm and positioned within the aneurysm cavity adjacent the first elongated shaft. The occlusive member may then be deployed within the aneurysm sac. As the occlusive member is deployed, it pushes the first elongated shaft outwardly towards the side of the aneurysm, and when fully deployed the occlusive member holds or "jails" the first elongated shaft between an outer surface of the occlusive member and the inner surface of the aneurysm wall.

The embolic element (such as embolic element 230) may then be delivered through the first elongated shaft to a position between the inner surface of the aneurysm wall and the outer surface of the occlusive member. For this reason, it may be beneficial to initially position the distal tip of the first elongated shaft near the dome (or more distal surface) of the aneurysm wall. This way, the "jailed" first elongated shaft will be secured by the occlusive member such that the embolic element gradually fills the open space in the aneurysm sac between the dome and the occlusive member. As described elsewhere herein, the filling of the embolic element pushes and compresses the occlusive member against the tissue surrounding the aneurysm neck as the space in the sac above the occlusive member is being filled from the dome to the neck. Also as described elsewhere herein, the compression of the occlusive member with the embolic element provides a "leveling or aneurysm filling indicator" which is not provided by conventional single plane imaging methods. The filling of the embolic element may complete, for example, when it occupies about 50-80% of the volume of the aneurysm.

III. Selected Devices, Systems, and Methods for Monitoring Deployment

Proper deployment of the embolic element 230 and the occlusive member 102 can be monitored and/or confirmed using one or more medical imaging techniques, such as fluoroscopy. FIGS. 4A-5B illustrate examples of various types of fluoroscopic images that may be employed by a physician at different stages of deployment to monitor the position of the occlusive member 102 within the aneurysm A, monitor the degree of filling of the aneurysm A with the embolic element 230, and/or confirm a degree of occlusion of the aneurysm A by the deployed system. As described in greater detail below, the devices and systems of the present technology may be configured to provide unique visual indicators that provide confirmation to the physician via one or more medical imaging techniques regarding a degree of occlusion of the aneurysm. As described in greater detail below, the visual indicators may include a particular change in shape of all or a portion of the occlusive member 102, a particular change in relative position of one or more radiopaque markers on the occlusive member 102 and/or delivery system (such as the conduit 116), a particular change in shape of the embolic element 230, and others.

Although the following discussion is made with reference to the two-dimensional images shown in FIGS. 4A-5B, the systems and methods of the present technology can be employed with three-dimensional imaging techniques. Moreover, FIGS. 4A-5B represent a two-dimensional image in which only a slice of the aneurysm (and devices therein) is visible. While in some cases the inner and outer layers of the occlusive member 102 (when such are present) may be distinguishable from one another in the radiographic image, in the present example the layers appear as one thick layer. As used herein, "proper deployment" or "successful deployment" may refer to (a) complete (e.g., greater than 80%) or substantially complete (e.g., greater than 50%) filling of the aneurysm A with the embolic element 230, (b) complete or substantially complete inversion or collapse of the occlusive member 102 onto itself over the neck N of the aneurysm A, (c) or both.

Figure 4A:
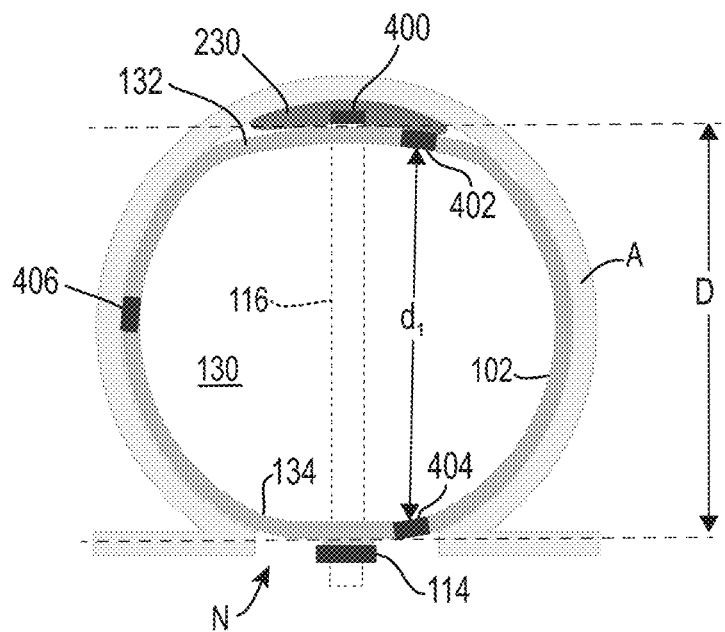
FIGS. 4A-5B show various types of images that may be employed to confirm and/or monitor deployment of the treatment system of the present technology.
Figure 4B:
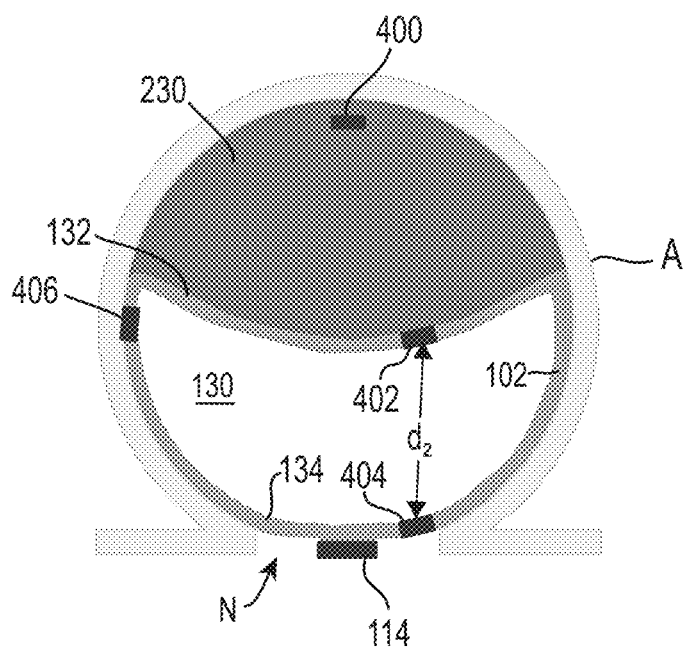
Figure 4C:
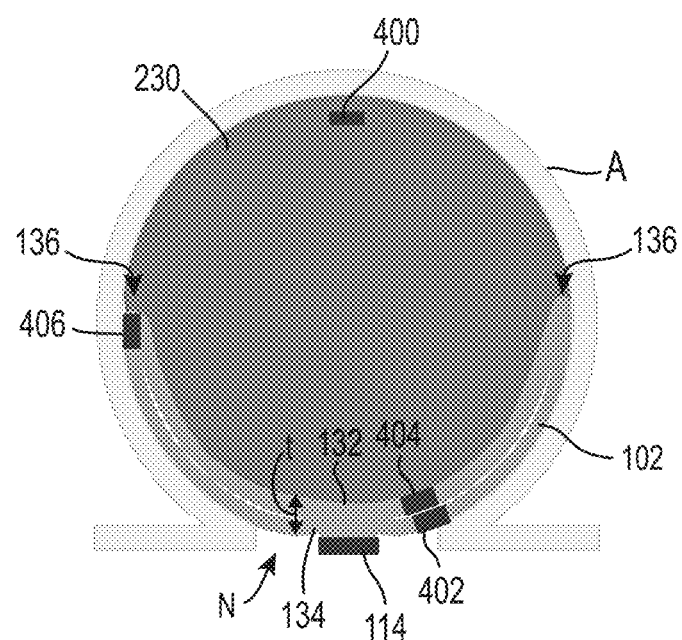

The occlusive member 102 may include one or more radiopaque markers, such as markers 402, 404, 406, and 114 (referred to collectively as "markers 401") shown in FIGS. 4A-4C. The markers 401 may be disposed about the occlusive member 102 in a specific spatial arrangement such that relative movement of the markers is indicative of a degree of stage of deployment of the occlusive member 102 and/or embolic element 230. The markers 401 may be positioned at any location along the occlusive member 102. For example, the occlusive member 102 may include one or more radiopaque markers 402 at or along its distal wall 132 (only one shown for ease of illustration), one or more radiopaque markers 404 at or along its proximal wall 134 (only one shown for ease of illustration), and one or more radiopaque markers 406 at or along the intermediate portion of the wall (only one shown for ease of illustration). Moreover, the coupler 114 of the occlusive member 102 may be radiopaque. The markers 401 may be positioned at one, some, or all of the layers of the occlusive member 102 (at least in those embodiments where the occlusive member 102 includes multiple layers). In some embodiments, the individual markers 401 may comprise a radiopaque band or clip coupled to the one or more struts, filaments, wires, etc. of the occlusive member 102. In some embodiments, the individual markers 401 may comprise a radiopaque material coated on or otherwise incorporated into the wall of the occlusive member 102. The individual markers 401 may have the same or different shapes, lengths, and/or profiles.

In some embodiments, in addition to or instead of having one or more markers 401, the occlusive member 102 itself may be partially or completely formed of a radiopaque material, such as one or more radiopaque wires. In the example depicted in FIGS. 4A-4C, the occlusive member 102 is formed of a radiopaque material and also includes radiopaque markers 402, 404, 406. The occlusive member 102 is formed of a plurality of drawn-filled tube ("DFT") wires, which comprise a core formed of a radiopaque material (such as platinum) surrounded by an outer non-radiopaque material (at least relative to the core material). The markers 402, 404, 406 are completely formed of a radiopaque material and thus have a higher density of radiopaque material. As such, the markers 402, 404, 406 appear darker than the occlusive member 102 in the images. In some embodiments, the occlusive member 102 may have a radiopacity that is different than the radiopacity of one or more of the markers 402, 404, 406 such that the wall of the occlusive member 102 wall and the marker(s) 406 can be distinguished from one another on the radiographic image. The wall of the occlusive member 102 may be more or less radiopaque than one or more of the markers 402, 404, 406.

In some embodiments, one or more components of the delivery system may include one or more radiopaque markers. For example, the conduit 116 may include one or more radiopaque markers positioned along its length. In the embodiment depicted in FIGS. 4A-4C, the conduit 116 may include a radiopaque marker 400 positioned at or near its distal end. The conduit 116 may have one or more additional markers (not shown) positioned along its length, such as along the length of the conduit 116 that extends through the interior volume 130 of the occlusive member 102.

As shown in FIG. 4A, when the occlusive member 102 is first deployed (e.g., allowed to self-expand) within the aneurysm, the radiopaque marker(s) 402, 404, 406 of the occlusive member 102 will be in a first position relative to one another, and to the radiopaque marker(s) of the conduit 116. By way of example, markers 402 and 404 are separated by a first distance $d_1$ when the occlusive member 102 is first deployed. As the embolic element 230 is conveyed through the conduit 116 and into the aneurysm sac, the occlusive member 102 may deform as described previously with respect to FIGS. 3A-3G. This deformation can cause the radiopaque marker(s) 401 carried by the occlusive member 102 to move to a second position relative to one another. For example, the physician may confirm progression of deployment by observing that markers 402 and 404 are now separated by a distance $d_2$. The radiopaque marker(s) 401 may also move relative to the radiopaque marker(s) 400 of the conduit 116, which may remain in the same or substantially the same place within the aneurysm. By comparing an image of the radiopaque markers 400 and/or 401 in the first relative positions and an image of the radiopaque markers 400 and/or 401 in the second relative positions, a clinician can visually confirm that the embolic element 230 has filled a certain percentage of the aneurysm A.

For example, according to some aspects of the technology, confirmation of sufficient filling of the aneurysm (i.e., 50% or greater) may be indicated by one or more distal wall markers 402 moving into close proximity to one or more proximal wall markers 404 and/or touching one or more proximal wall markers 404. Because the embolic element 230 applies a generally uniform pressure across the distal wall 132 and pushes downwardly towards the neck N as it fills in the space between the occlusive member 102 and the aneurysm wall, the movement of one or more distal wall markers 402 to a position adjacent a proximal wall marker 404 indicates to a physician that the aneurysm A is substantially filled (e.g., 50% or greater) with the embolic element 230. This relative positioning also indicates that the distal wall 132 is now providing additional occlusion at the neck N of the aneurysm and that the occlusive member 102 is in its second expanded shape. In some embodiments, the coupler 114 may be used as the proximal indicator instead of or in addition to the one or more proximal markers 404.

In some embodiments, confirmation of sufficient filling of the aneurysm (i.e., 50% or greater) may be indicated by one or more distal wall markers 402 moving away from the conduit marker 400 (or marker affixed to another component of the delivery system) by a predetermined distance. For example, when the occlusive member 102 is in the first expanded state or shape (FIG. 4A) the distal wall marker 402 may be adjacent the conduit marker 400. In the second expanded state or shape (FIG. 4C), the distal wall marker 402 may be separated from the conduit marker 400 by a distance that is generally equivalent to a diameter D of the occlusive member 102 in its expanded state while initially positioned in the aneurysm A. As explained above, such relative positioning of one or more distal wall markers 402 and conduit marker 400 indicates to a physician that the aneurysm A is substantially filled (e.g., 50% or greater) with the embolic element 230. This relative positioning also indicates that the distal wall 132 is now providing additional occlusion at the neck N of the aneurysm and that the occlusive member 102 is in its second expanded shape.

In some embodiments, one or more intermediate markers 406 may be used to confirm and/or monitor deployment. For example, one or more intermediate markers 406 may be positioned at or near a desired inversion plane of the occlusive member 102. In the present example using a generally spherical occlusive member 102 that deforms to assume a bowl shape, the inversion plane is at or near a midline of the occlusive member 102 in its expanded state. This is because, in a fully inverted state, the distal half of the occlusive member 102 will lie within/conform to the proximal half of the occlusive member 102 (as shown in FIG. 4C). As such, the midline of the occlusive member 102 is the desired plane of inversion. The occlusive member 102 may be radiopaque (as shown in FIGS. 4A-4C), but to a lesser extent than the intermediate marker(s) 406 such that the occlusive member 102 wall and the marker(s) 406 can be distinguished from one another on the radiographic image. As such, an image showing the top edge 136 (FIG. 4C) of the occlusive member 102 adjacent or at the intermediate marker(s) 406 may indicate that the aneurysm A is substantially filled (e.g., 50% or greater) with the embolic element 230. This relative positioning also indicates that the distal wall 132 is now providing additional occlusion at the neck N of the aneurysm and that the occlusive member 102 is in its second expanded shape.

The change in shape of the occlusive member 102 and/or change in position of different portions of the occlusive member 102 relatively to one another may also indicate proper deployment. As previously discussed, the occlusive member 102 assumes a first expanded shape when initially deployed and has a second expanded shape after deformation by the embolic element 230. In several embodiments, the second expanded shape represents a partially or completely inverted from of the first expanded shape, which can be confirmed on the radiographic image by observing the changing outline of the occlusive member 102. For instance, in the present example where the occlusive member 102 has a first expanded shape that is generally spherical, an image showing a C-shape (as shown in FIG. 4C) may indicate that the desired filling and/or deployment is complete. In a three-dimensional image, the second expanded shape may have a bowl shape. In some embodiments, confirmation of complete or substantially complete deployment may be indicated by the distal wall 500 being within a predetermined distance of the proximal wall 502.

In some embodiments, proper deployment may be confirmed by observing a distance between the inverted wall (here, distal wall 132) and the relatively stationary wall (here, proximal wall 134). As shown in FIG. 4C, when the distal wall 132 collapses down onto or near the proximal wall 134, the occlusive member 102 presents on the image as having twice the thickness at the proximal portion. Moreover, as the occlusive member 102 inverts, the density of the radiopaque material doubles, and thus the doubled-over portions of the occlusive member 102 appear darker on the image.

Figure 5A:
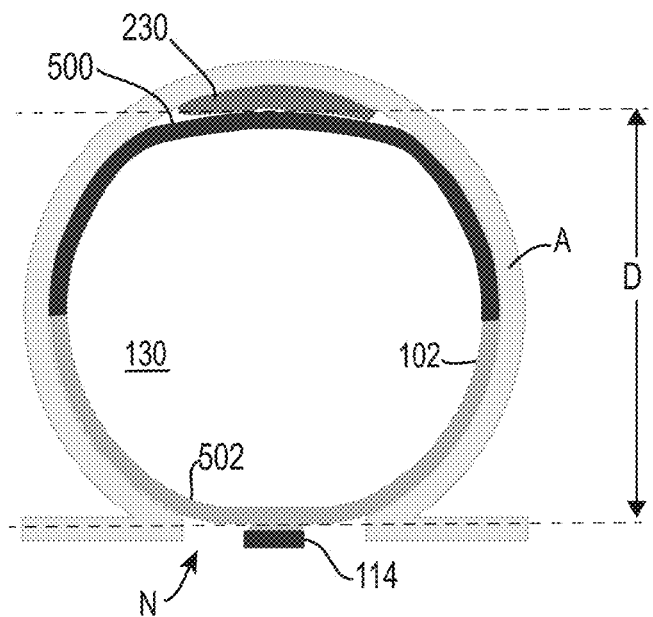
Figure 5B:
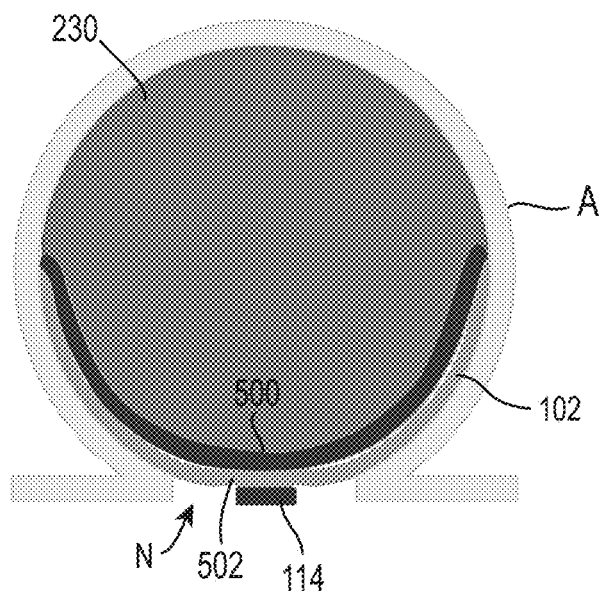

As shown in FIGS. 5A and 5B, in some embodiments, certain portions of the occlusive member 102 may be coated with a radiopaque material such that change in shape or orientation of those portions indicates a desired position of the occlusive member 102. For example, as shown in FIG. 5A, a distal-most half 500 of the occlusive member 102 may be coated with a radiopaque material while a proximal-most half 502 may not be coated or may otherwise be less radiopaque than the distal half 500. As such, confirmation of complete or substantially complete deployment may be indicated by the more radiopaque distal wall 500 being adjacent the proximal wall 502. For example, confirmation of complete or substantially complete deployment may be indicated by the distal wall 500 being within a predetermined distance of the proximal wall 502. Confirmation may also be gleaned from the distal wall 500 changing in shape from flat or convex (towards the dome) of the aneurysm A to concave.

A shape of the embolic element 230 may also provide an indication of deployment progress. For example, the shape of the lower (closer to the neck N) perimeter of the aneurysm A can be indicative of a degree of filling of the aneurysm with the embolic element 230 and/or degree of deformation of the occlusive member 102. As most aneurysms have a generally spherical or globular shape, a lower boundary of the embolic element 230 may have a decreasing radius of curvature as more is injected and more of the occlusive member 102 inverts. For example, in FIG. 4B, when the aneurysm A is partially filled with the embolic element 230 and the occlusive member 102 is only partially collapsed or inverted, the distal wall 132 has a first radius of curvature. In FIG. 4C, when the aneurysm A is substantially completely or completely filled, the distal wall 132 has a radius of curvature less than the radius of curvature of the distal wall 132 in the partially deformed state.

Additionally or alternatively, the degree of deployment of the occlusive member 102 and/or degree of filling of the aneurysm A can be further determined by injecting contrast into the parent blood vessel and imaging the aneurysm to determine how much of the contrast enters the aneurysm cavity. The shape of the The devices, systems, and methods of the present technology may be particularly beneficial over conventional devices for two-dimensional imaging. In two dimensional imaging (such as fluoroscopy), the image may reflect only a slice or elevational view of the aneurysm (and device or substance therein). As such, any voids or gaps in filling may not be apparent in the slice because the image slice does not transect the void within the aneurysm A, or the cross-section or elevational view of the stagnated area may take on different shapes depending on how the image is observed. A physician may have to take a plurality of images to determine a general amount of filling in the aneurysm. In contrast, the occlusion members 102 of the present technology have a unique shape that dynamically adjusts to the introduction of an embolic element 230 in a predictable, measurable way that indicates a degree of filling of the embolic element 230 in a single two-dimensional radiographic image.

The devices, systems, and methods disclosed herein include confirming and/or observing various stages of deployment of the system in an aneurysm, including complete or substantially complete deployment, using one, some, or all of the methods disclosed above.

IV. Selected Embodiments

Figure 6:
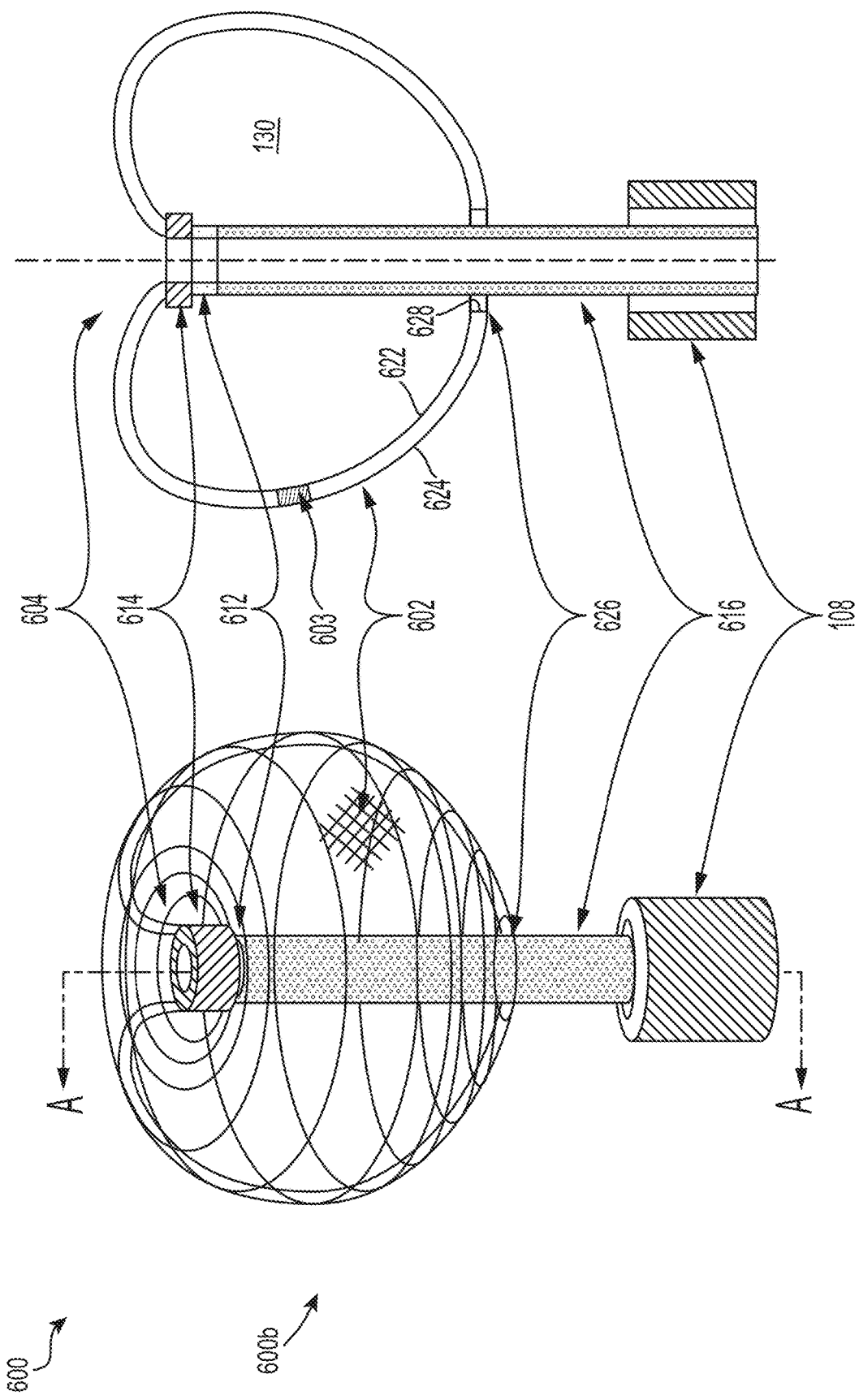
FIG. 6 shows a system for treating an aneurysm in accordance with the present technology.

FIG. 6 shows the distal portion of a treatment system 600 for treating an aneurysm in accordance with the present technology. The treatment system 600 may be a portion of a system that also includes an embolic kit (not shown). The embolic kit may be substantially the same as the embolic kit 200 described above. As shown in FIG. 6, the treatment system 600 may comprise an occlusive member 602 (shown in an expanded state) detachably coupled to a delivery system, and the delivery system may be configured to intravascularly position the occlusive member 602 within an aneurysm. In some embodiments, the treatment system 600 may be configured to deliver the embolic element (and/or one or more precursors thereof) to the aneurysm. Additionally or alternatively, the system may include a separate delivery system (not shown) for delivering the embolic element (and/or one or more precursors thereof) to the aneurysm cavity.

Similar to treatment system 100, the treatment system 600 has a proximal portion (not shown) configured to be extracorporeally positioned during treatment and a distal portion 600b configured to be intravascularly positioned within a blood vessel (such as an intracranial blood vessel) at a treatment site at or proximate an aneurysm. The treatment system 600 may include a handle at the proximal portion, the occlusive member 602 at the distal portion 600b, and a plurality of elongated shafts or members extending between the proximal and distal portions. In some embodiments, such as that shown in FIG. 6, the treatment system 600 may include a first elongated shaft (such as a guide catheter or balloon guide catheter) (not depicted), a second elongated shaft 108 (such as a microcatheter) configured to be slidably disposed within a lumen of the first elongated shaft, and an elongated member 616 configured to be slidably disposed within a lumen of the second elongated shaft 108. In contrast to the delivery system of treatment system 100, the elongated member 616 also functions as the conduit. As such, the treatment system 600 does not include a separate elongated member 616 and conduit. In some embodiments, the treatment system 600 does not include the first elongated shaft and only includes the second elongated shaft 108.

A distal end of the occlusive member 602 may be detachably coupled to a distal end of the elongated member 616. For example, the elongated member 616 may include a first coupler 612 at its distal end, and the occlusive member 602 may include a second coupler 614 configured to detachably couple with the first coupler 612. The elongated member 616 may be configured to deliver the embolic element (and/or one or more precursors thereof) through one or more components of the delivery system (e.g., the first or second elongated shafts 109, 108) to a position at the exterior of the occlusive member 602. As such, the embolic element may be positioned between the occlusive member 102 and an inner wall of the aneurysm cavity, as described in greater detail below.

According to some embodiments, the second elongated shaft 108 is generally constructed to track over a conventional guidewire in the cervical anatomy and into the cerebral vessels associated with the brain and may also be chosen according to several standard designs that are generally available. Accordingly, the second elongated shaft 108 can have a length that is at least 125 cm long, and more particularly may be between about 125 cm and about 175 cm long. In some embodiments, the second elongated shaft 108 may have an inner diameter of about 0.015 inches (0.0381 cm), 0.017 inches (0.043 cm), about 0.021 inches (0.053 cm), or about 0.027 inches (0.069 cm). Other designs and dimensions are contemplated.

The elongated member 616 can be movable within the first and/or second elongated shafts to position the occlusive member 602 at a desired location. The elongated member 616 can be sufficiently flexible to allow manipulation, e.g., advancement and/or retraction, of the occlusive member 602 through tortuous passages. Tortuous passages can include, for example, catheter lumens, microcatheter lumens, blood vessels, urinary tracts, biliary tracts, and airways. The elongated member 616 can be formed of any material and in any dimensions suitable for the task(s) for which the system is to be employed. In some embodiments, the elongated member 616 may comprise any other suitable form of shaft such as an elongated tubular shaft.

In some embodiments, the elongated member 616 can comprise stainless steel, nitinol, cobalt-chrome, or other metal or alloy. In some embodiments, the elongated member 616 can be surrounded over some or all of its length by a coating, such as, for example, polytetrafluoroethylene. The elongated member 616 may have a diameter that is generally constant along its length, or the elongated member 616 may have a diameter that tapers radially inwardly, along at least a portion of its length, as it extends in a distal direction.

C. Selected Examples of Occlusive Members

Referring still to FIG. 6, the occlusive member 602 may comprise an expandable element having a low-profile or constrained state while positioned within a catheter (such as the second elongated shaft 108) for delivery to the aneurysm and an expanded state in which the expandable element is configured to be positioned within an aneurysm (such as a cerebral aneurysm). According to some embodiments, the occlusive member 602 may comprise a mesh formed of a plurality of braided filaments that have been heat-set to assume a predetermined shape enclosing an interior volume 130 when the mesh is in an expanded, unconstrained state. Example shapes include a globular shape, such as a sphere, a prolate spheroid, an oblate spheroid, and others. As depicted in the cross-sectional view in FIG. 6, the mesh may have inner and outer layers 622, 624 that have distal ends fixed relative to one another at the second coupler 614 and meet distally at a proximal fold 628 surrounding a proximal aperture 626. While the inner and outer layers 622, 624 are depicted spaced apart from one another along their lengths, the inner and outer layers 622, 624 may be in contact with one another along all or a portion of their lengths. For example, the inner layer 622 may press radially outwardly against the outer layer 624. In some embodiments, the occlusive member 602 may be formed of a single layer or mesh or braid.

The elongated shaft 616 may be configured to be slidably positioned through some or all of the second coupler 614, the interior volume 130 of the expanded mesh, and the opening 626. Because the occlusive member 602 is coupled to the elongated shaft 616 at its distal end (e.g., via the first and second couplers 612, 614), axial movement of the elongated shaft 616 causes axial movement of at least the distal portion of the occlusive member 602. The proximal portion of the occlusive member 602 remains free to slide along the elongated shaft 616 via the proximal aperture 626. In some embodiments, when the occlusive member 602 is loaded in the elongated member 616, the occlusive member 602 is positioned around the elongated member 616, between the elongated member 616 and the second elongated shaft 108.

The inner and outer layers 622 and 624 may conform to one another at the distal portion (for example as shown in FIG. 5) to form a curved distal surface. For example, at least at the distal portion of the occlusive member 602, the inner and outer layers 622 and 624 may extend distally and radially inwardly, towards the aperture 626. In some embodiments, the outer and/or inner layers 622 and 624 extend distally and radially outwardly from the fold 628 at the aperture 626, then extend distally and radially inwardly up to ridge, then proximally to the second coupler 614 to create a detent or recess 604 at the distal end of the occlusive member 602. For example, the distal surface of the occlusive member 602 may be concave towards the dome of the aneurysm. The distal recess 604 may be beneficial for delivering the embolic element 230 in that it creates a small gap between the distal surface of the occlusive member 602 and the dome of the aneurysm A (see, for example, FIG. 7B).

The occlusive member 602 and/or layers thereof may be curved along its entire length, or may have one or more generally straight portions. In some embodiments, the curved surface transitions to a flat or substantially flat, distal-most surface that surrounds the aperture 626. In some embodiments, the curved surface transitions to a distal-most surface that surrounds the aperture 626 and has a radius of curvature that is greater than the average radius of curvature of the rest of the occlusive member 602. Having a flat or substantially flat distal surface, or a distal surface with a radius of curvature that is greater than the average radius of curvature of the rest of the occlusive member 602, may be beneficial for delivering the embolic element 230 in that it creates a small gap between the distal surface of the occlusive member 602 and the dome of the aneurysm A. In some embodiments, the surface of the occlusive member 602 surrounding the aperture 626 is curved and/or has generally the same radius of curvature as the remainder of the occlusive member 602.

In any case, the inner layer 624 may have a shape that substantially conforms to the shape of the outer layer 624, or the inner and outer layers 622, 624 may have different shapes. For example, the inner layer 622 may have a diameter or cross-sectional dimension that is less than the outer layer 624 (for example, as shown in FIG. 1D). Such a configuration may be beneficial in that the embolic element 230 experiences less resistance, at least initially, when pushing the distal wall of the occlusion member 602 downwardly towards the neck (as described in greater detail below).

In any case, both the proximal portion and the distal portion of the mesh can form generally closed surfaces. However, unlike at the second coupler 614 at the distal portion of the mesh, the portion of the filaments at or near the fold 628 at the proximal portion of the mesh can move relative to one another. As such, the distal portion of the mesh has both the properties of a closed end and also some properties of an open end (like a traditional stent), such as some freedom of movement of the proximal-most portions of the filaments and an opening through which the elongated shaft 616, a guidewire, guidetube, or other elongated member may pass through.

In some embodiments, each of the plurality of filaments have a first end positioned at the distal portion of the mesh and a second end also positioned at the distal portion of the mesh (for example, at the second coupler 614). Each of the filaments may extend from its corresponding first end distally to ridge, then proximally along the body of the mesh to the fold 628, invert, then extend distally along the mesh body to the ridge, then proximally to its corresponding second end at the distal portion of the mesh. As such, each of the plurality of filaments have a first length that forms the inner layer 622 of the mesh, a second length that forms the outer layer 624 of the mesh, and both first and second ends fixed at the distal portion of the mesh. In some embodiments, the occlusive member 602 may comprise a mesh formed of a single layer, or a mesh formed of three or more layers.

In some embodiments, the proximal and/or distal end surface of the mesh is completely closed (i.e., does not include an aperture). In some embodiments the filaments are fixed relative to the at both the proximal and distal ends of the occlusive member 602 and the elongated member 616 is configured to be slidably disposed through each of the proximal and distal hubs.

In some embodiments, the occlusive member 602 and/or mesh may include a preferential bending region 604 at which the occlusive member 602 and/or mesh is configured to preferentially flex or bend when subject to inverting forces (such as that exerted by the embolic element 230, as described in greater detail below). The bending region 604 may form a continuous band around the circumference of the occlusive member 602, or it may be at select locations about the circumference of the occlusive member 602, all located at generally the same axial location along the mesh. In those embodiments in which the occlusive member 602 comprises multiple layers, none, some, or all of the layers may include the bending region 604. The bending region 604 may comprise, for example, a thinned portion of the mesh that is generally weaker than the surrounding portions and thus more likely to bend under stress. The bending region 604 may also be formed by heat setting the mesh in the inverted or collapsed state such that the mesh preferentially inverts at the desired level.

The mesh forming the occlusive member 602 may be formed of metal wires, polymer wires, or both, and the wires may have shape memory and/or superelastic properties. The mesh may be formed of 24, 32, 36, 48, 64, 72, 96, 128, or 144 filaments. The mesh may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments of the braided mesh may have the same diameter. For example, in some embodiments, all of the filaments have a diameter of about 0.001 inches. In some embodiments, some of the filaments may have different cross-sectional diameters. For example, some of the filaments may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling-out the braid matrix density.

The occlusive member 602 can have different shapes and sizes in an expanded, unconstrained state. For example, the occlusive member 602 may have a bullet shape, a barrel-shape, an egg shape, a dreidel shape, a bowl shape, a disc shape, a cylindrical or substantially cylindrical shape, a barrel shape, a chalice shape, etc.

D. Selected Examples of Embolic Kits

Figure 7A:
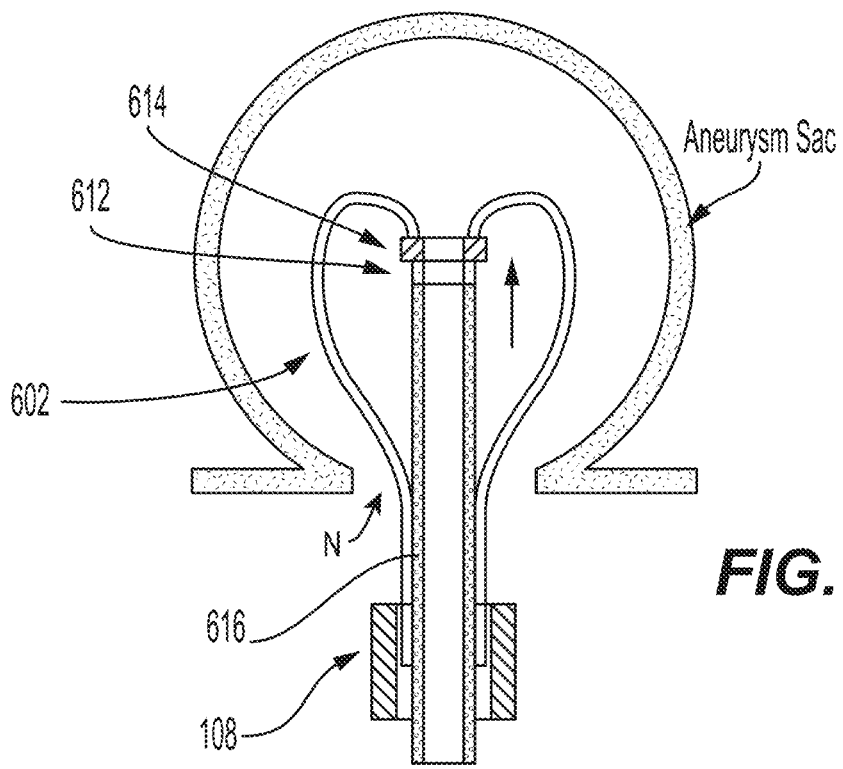
FIGS. 7A-7J depict an example method of treating an aneurysm with the treatment systems of the present technology.
Figure 7B:
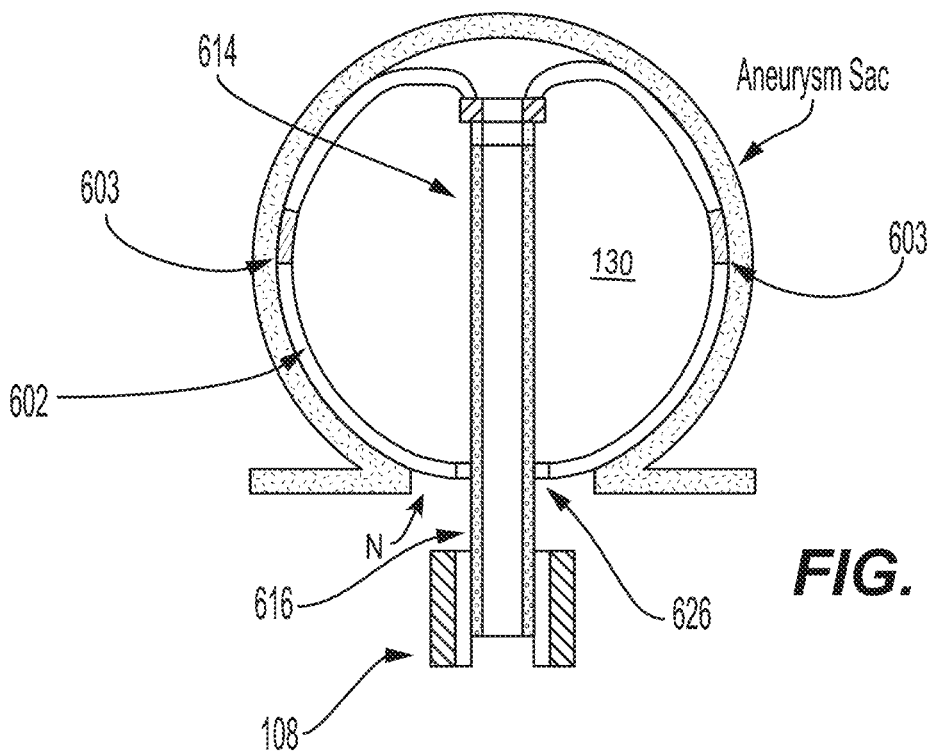
Figure 7C:
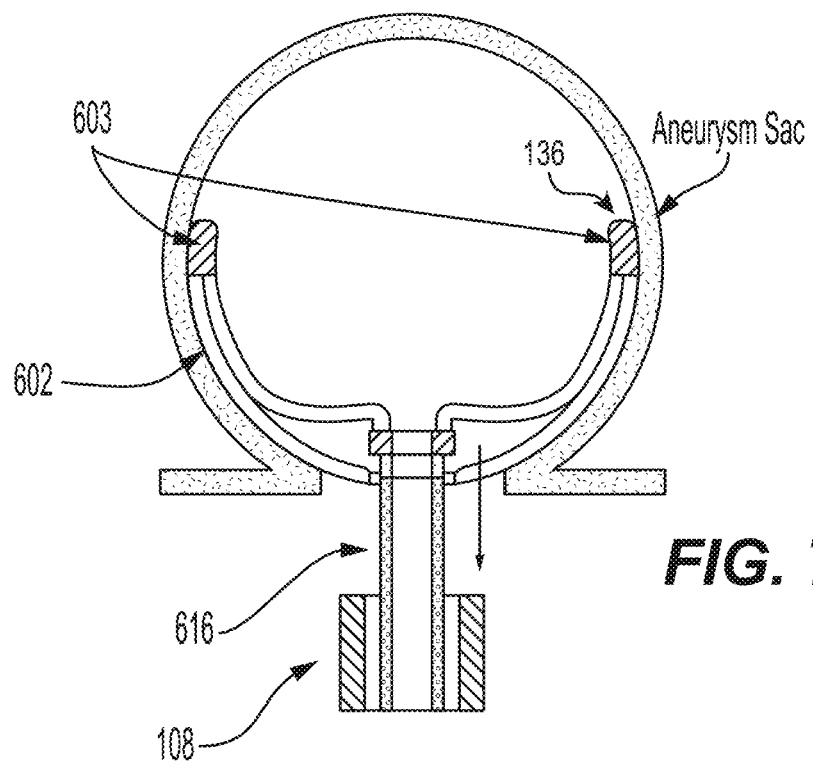
Figure 7D:
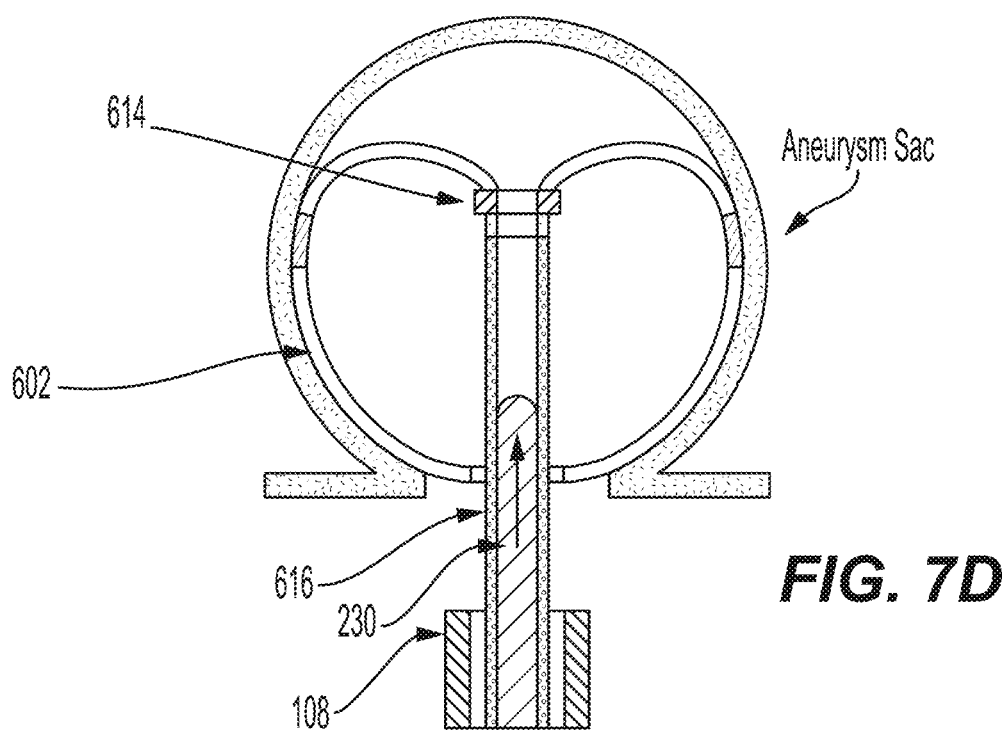
Figure 7E:
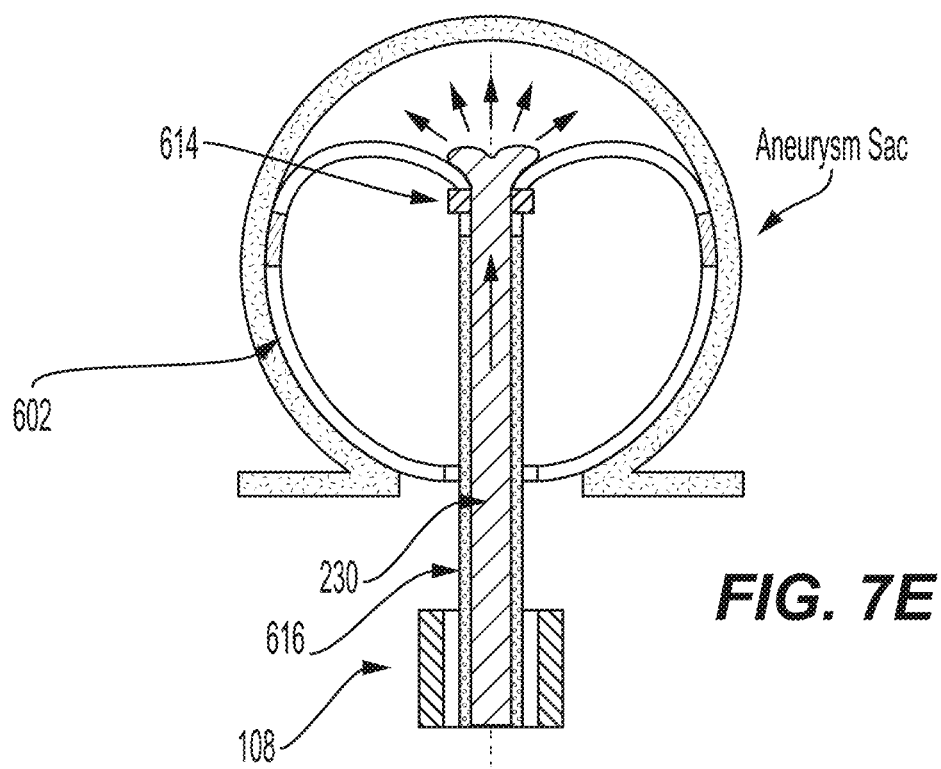
Figure 7F:
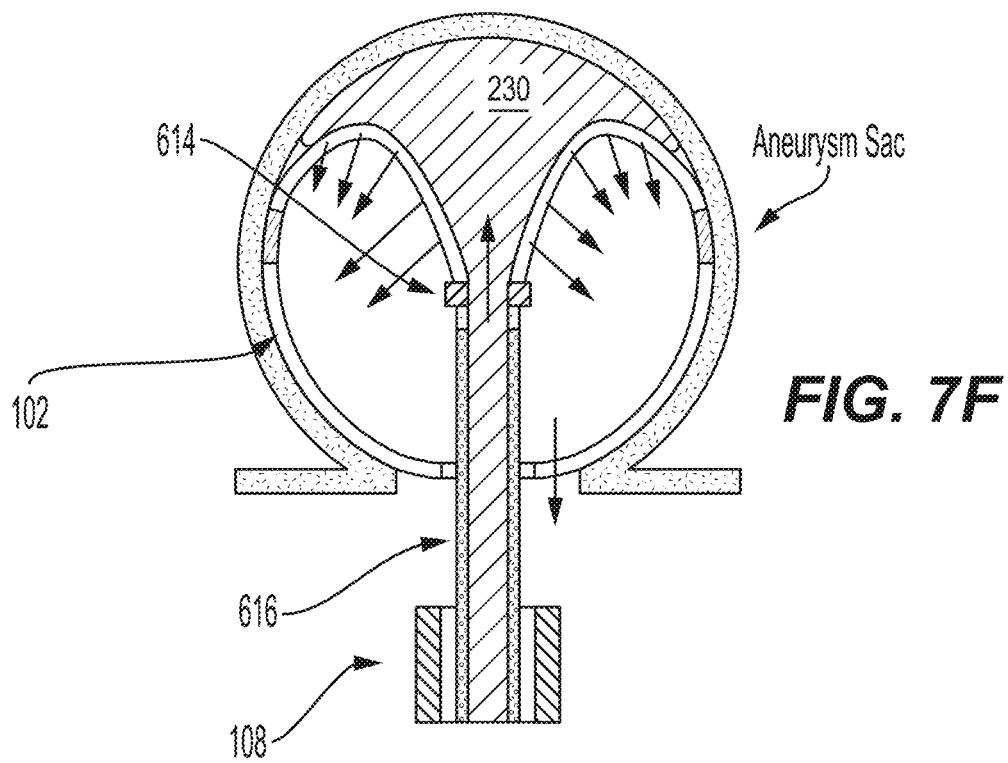
Figure 7G:
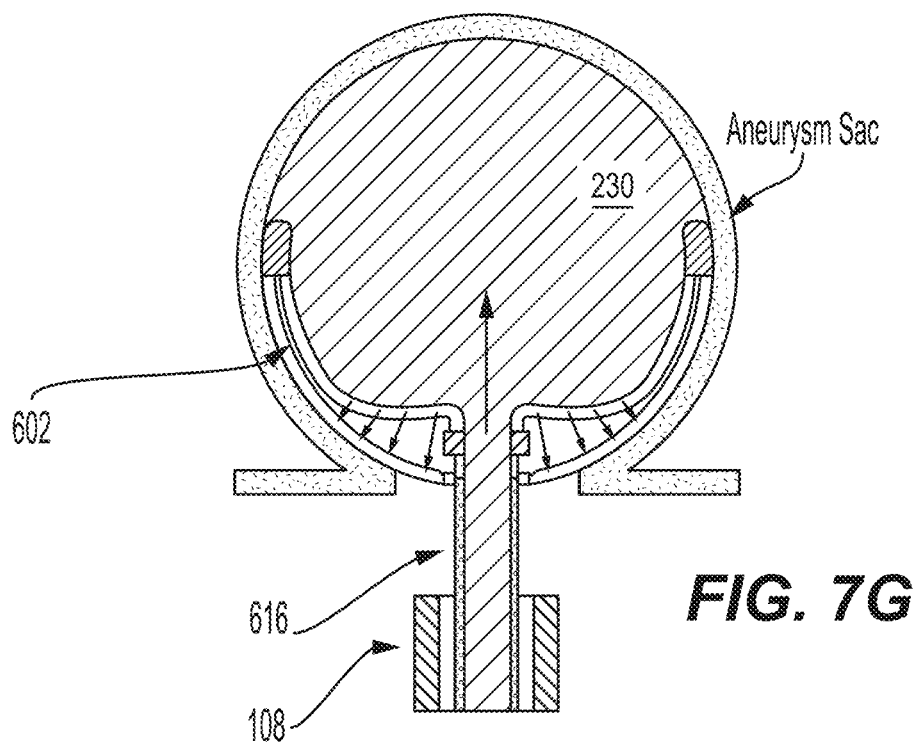
Figure 7H:
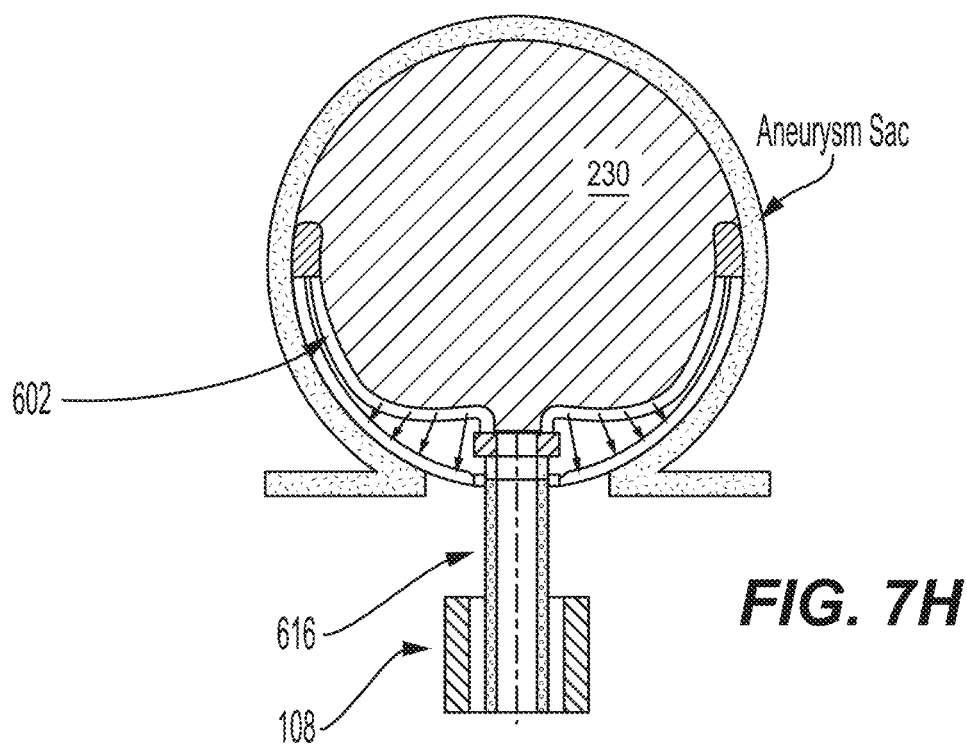
Figure 7I:
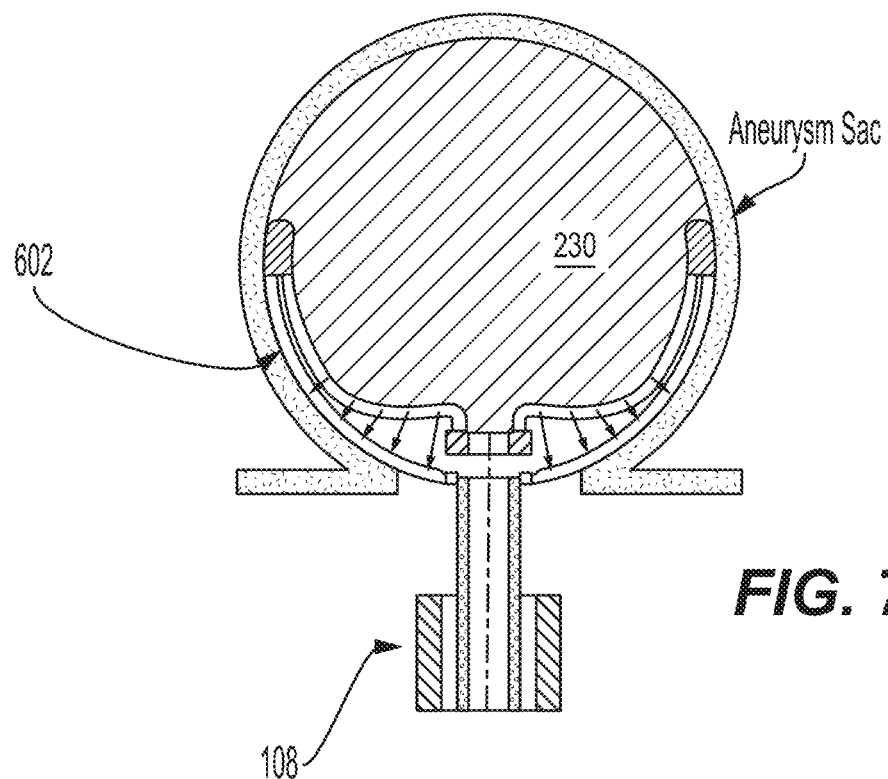
Figure 7J:
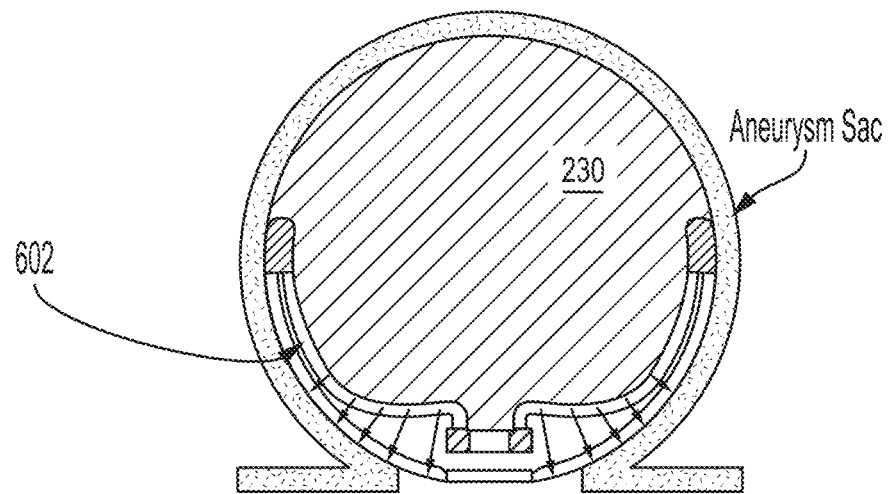

The embolic kit for use with the treatment system shown in FIGS. 6-7J may be substantially similar to the embolic kit 200 described above.

E. Selected Methods of Deployment

FIGS. 7A-7J depict an example method of treating an aneurysm with the treatment systems of the present technology. To begin, a physician may intravascularly advance the second elongated shaft 108 towards an intracranial aneurysm (or other treatment location such as any of those described herein) with the occlusive member 602 in a low-profile state. As shown in FIG. 7A, the second elongated shaft 108 may be positioned at or just proximal of the neck. Alternatively, a distal portion of the second elongated shaft 108 may be advanced through a neck N of the aneurysm A to locate a distal opening of the second elongated shaft 108 within an interior cavity of the aneurysm A. In either case, the elongated member 616 may be advanced distally through the neck N and into the aneurysm cavity (if not already in the aneurysm cavity), thereby pulling the distal end of the occlusive member 602 with it. As the occlusive member 602 is released from its constrained state within the second elongated shaft 108, the occlusive member 602 expands towards the first expanded state, as shown in FIG. 7B. In the first expanded state, the occlusive member 602 may assume a predetermined shape that encloses an internal volume 130. In this first expanded state, the occlusive member 602 may generally conform to the shape of the aneurysm A.

Prior to delivering the embolic agent 230, the physician may pull the elongated member 616 proximally to check the positioning of the occlusive member 602 in the aneurysm A. As depicted in FIGS. 7B and 7C, for example, the elongated member 616 may be pulled proximally to force the distal wall towards the neck N and proximal wall. Because of the bending region(s) 603, the occlusive member 602 may preferentially fold and develop a distal edge at the bending regions 603. The ability to check the position of the occlusive member 602 in its collapsed state before delivering the embolic element 230 may be beneficial, especially in wide-necked aneurysms, as the initial approach into the aneurysm may be too steep such that the distal edge 136 (see FIG. 7C), once the occlusive member 602 is fully collapsed or inverted, is near or aligned with the neck of the aneurysm A. In those cases, the occlusive member 602 may not fully cover the neck N, and thus will not be sufficiently anchored in the aneurysm A. It will be appreciated that the elongated member 616 may be used to check the positioning of the occlusive member 602 even in those embodiments where the occlusive member 602 does not have a bending region 603.

As shown in FIGS. 7D-7H, the embolic element 230 may be delivered through the elongated member 616 to a space between the occlusive member 602 and an inner surface of the aneurysm wall W. In some embodiments, the method includes mixing the first and second precursor materials 203, 205 (FIG. 2) to form the embolic element 230. Mixing of the first and second precursor materials 203, 205 may occur prior to introducing the embolic element 230 to the treatment system 100 and/or during delivery of the embolic element through the elongated member 616 to the aneurysm. In a particular example, the first precursor material 203 is loaded into one of the barrels 214, the second precursor materials 205 is loaded into the other barrel 214, and the mixing syringes 208 are coupled via the coupler 210. To mix the first and second precursor materials 203, 205, the plungers 212 are alternately depressed, thereby causing the first and second precursor materials 203, 205 to move repeatedly from one barrel 214 to the other barrel 214. After suitably mixing the precursor materials, the resulting embolic element 230 can be loaded into the barrel 220 of the injection syringe 216. The injection syringe 216 may then be coupled to a proximal end of the elongated member 616 to deliver the embolic element 230 through the elongated member 616 and into the aneurysm A. As the embolic element 230 passes through the lumen of the elongated member 616, chemical crosslinking of the biopolymer can continue to occur.

Still with reference to FIGS. 7D-7H, as the embolic element 230 is delivered between the dome of the aneurysm A and the distal portion of the wall of the occlusive member 602, pressure builds between the aneurysm wall W and the occlusive member 602. When the forces on the occlusive member 602 reach a threshold level, the embolic element 230 pushes the distal wall downwardly towards the neck N of the aneurysm A. If desired, the elongated member 616 may be pulled proximally while the embolic element 230 is delivered and/or between different injections of the embolic element 230, which encourages inversion of the occlusive member 602.

As detailed above, the embolic element 230 exerts a substantially uniform pressure across the distal surface of the occlusive member 602 that collapses the occlusive member 602 inwardly on itself (with or without the help of the elongated member 616). The pressure and inversion of the distal portion of the wall creates an annular fold 136 that defines the distal-most edge of the occlusive member 602. As the occlusive member 602 continues to invert, the position of the fold moves towards the neck N, which continues until a distal-most half of the occlusive member 602 has inverted. Moreover, as the occlusive member 602 collapses, a distance between the wall at the distal portion and the wall at the proximal portion decreases, and thus the internal volume 130 of the occlusive member 602 also decreases. As the occlusive member 602 collapses, the elongated member 616 may be held stationary, advanced distally, and/or retracted proximally.

During and after delivery of the embolic element 230, none or substantially none of the embolic element 230 migrates through the pores of the occlusive member 602 and into the internal volume 130. Said another way, all or substantially all of the embolic element 230 remains at the exterior surface or outside of the occlusive member 602. Compression of the occlusive member with the embolic element 230 provides a real-time "leveling" or "aneurysm-filling indicator" to the physician under single plane imaging methods (such as fluoroscopy) so that the physician can confirm at what point the volume of the aneurysm is completely filled. Additional details regarding devices, systems, and methods for monitoring and/or confirming deployment are described above with reference to FIGS. 4A-5B. It is beneficial to fill as much space in the aneurysm as possible, as leaving voids within the aneurysm sac may cause delayed healing and increased risk of aneurysm recanalization and/or rupture. While the scaffolding provided by the occlusive member 602 across the neck helps thrombosis of blood in any gaps and healing at the neck, the substantial filling of the cavity prevents rupture acutely and does not rely on the neck scaffold (i.e., the occlusive member 602). Confirmation of complete or substantially complete aneurysm filling under single plane imaging cannot be provided by conventional devices.

Once delivery of the embolic element 230 is complete, the elongated member 616 may be withdrawn. In some embodiments, the embolic element 230 may fill greater than 40% of the aneurysm sac volume. In some embodiments, the embolic element 230 may fill greater than 50% of the aneurysm sac volume. In some embodiments, the embolic element 230 may fill greater than 60% of the aneurysm sac volume. In some embodiments, the embolic element may fill greater than 65%, 70%, 75%, 80%, 85%, or 90% of the aneurysm sac volume.

FIG. 7I shows a second expanded state of the occlusive member 602, shown in cross-section, with the embolic element 230 occupying the remaining volume of the aneurysm A. As shown, the embolic element 230 may be delivered until the occlusive member 602 is fully-collapsed such that the occlusive member 602 has substantially no internal volume. In the second expanded state, the occlusive member 602 may form a bowl shape that extends across the neck of the aneurysm A. The wall of the occlusive member 602 at the distal portion may now be positioned in contact with or immediately adjacent the wall of the occlusive member 602 at the proximal portion. In some instances, because of the presence of the second coupler 614, a small gap may remain between portions of the distal wall and the proximal wall when the occlusive member 602 is in its second or collapsed state.

Collapse of the occlusive member 602 onto itself, towards the neck N of the aneurysm, may be especially beneficial as it doubles the number of layers across the neck and thus increases occlusion at the neck N. For example, the distal wall 132 collapsing or inverting onto the proximal wall may decrease the porosity of the occlusive member 602 at the neck N. In those embodiments where the occlusive member 602 is a mesh or braided device such that the distal wall has a first porosity and the proximal wall has a second porosity, deformation of the distal wall onto or into close proximity within the proximal wall decreases the effective porosity of the occlusive member 602 over the neck N. The resulting multi-layer structure thus has a lower porosity than the individual first and second porosities. Moreover, the embolic element 230 along the distal wall provides additional occlusion. In some embodiments, the embolic element 230 completely or substantially completely occludes the pores of the adjacent layer or wall of the occlusion member 602 such that blood cannot flow past the embolic element 230 into the aneurysm cavity. It is desirable to occlude as much of the aneurysm as possible, as leaving voids of gaps can allow blood to flow in and/or pool, which may continue to stretch out the walls of aneurysm A. Dilation of the aneurysm A can lead to recanalization and/or herniation of the occlusive member 602 and/or embolic element 230 into the parent vessel and/or may cause the aneurysm A to rupture. Both conditions can be fatal to the patient.

In those embodiments where the wall of the occlusive member 602 comprises an inner and outer layer, the deformed or second shape of the occlusive member 602 forms four layers over the neck N of the aneurysm A In those embodiments where the wall of the occlusive member 602 comprises a single layer, the deformed or second shape of the occlusive member 602 forms two layers over the neck N of the aneurysm A As previously mentioned, the neck coverage provided by the doubled layers provides additional surface area for endothelial cell growth, decreases the porosity of the occlusive member 602 at the neck N (as compared to two layers or one layer), and prevents herniation of the embolic element 230 into the parent vessel. During and after delivery, the embolic element 230 exerts a substantially uniform pressure on the occlusive member 602 towards the neck N of the aneurysm A, thereby pressing the portions of the occlusive member 602 positioned adjacent the neck against the inner surface of the aneurysm wall such that the occlusive member 602 forms a complete and stable seal at the neck N.

In some embodiments, the elongated member 616 may be moved proximally and distally to move the distal wall of the occlusive member 602 to re-distribute the embolic element 230 around the occlusive member 602 and the aneurysm wall. As a result, the occlusive member 602 will be locked and prevent migration after treatment. In this case, the occlusive member 602 may not need to fill the sac completely.

As shown in FIGS. 7I-7J, the first coupler 612 may be detached from the second coupler 614 and the elongated member 616 and second elongated shaft 108 may be withdrawn, thereby leaving the occlusive member 602 and embolic element 230 implanted within the aneurysm A.

Over time natural vascular remodeling mechanisms and/or bioabsorption of the embolic element 230 may lead to formation of a thrombus and/or conversion of entrapped thrombus to fibrous tissue within the internal volume of the aneurysm A. These mechanisms also may lead to cell death at a wall of the aneurysm and growth of new endothelial cells between and over the filaments or struts of the occlusive device 602. Eventually, the thrombus and the cells at the wall of the aneurysm may fully degrade, leaving behind a successfully remodeled region of the blood vessel.

In some embodiments, contrast agent can be delivered during advancement of the occlusive member 602 and/or embolic element 230 in the vasculature, deployment of the occlusive member 602 and/or embolic element 230 at the aneurysm A, and/or after deployment of the occlusive member 602 and/or embolic element 230 prior to initiation of withdrawal of the delivery system. The contrast agent can be delivered through the second elongated shaft 108, the elongated member 616, or through another catheter or device commonly used to delivery contrast agent. The aneurysm (and devices therein) may be imaged before, during, and/or after injection of the contrast agent, and the images may be compared to confirm a degree of occlusion of the aneurysm.

Conclusion

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system comprising:
   an elongate shaft defining a lumen;
   an elongate member slidably disposed within the lumen of the elongate shaft, the elongate member having a proximal end region and a distal end region, wherein the distal end region is configured to be intravascularly positioned at or within an aneurysm cavity; and
   an occlusive member constrained within the lumen of the shaft, the occlusive member including a proximal end portion having an opening and a distal end portion detachably coupled to the distal end region of the elongate member, wherein the elongate member extends through the opening, and wherein the occlusive member comprises one or more preferential bending regions about all or a portion of the circumference of the occlusive member, and
   wherein pushing the elongate member from a distal opening in the elongate shaft pulls the occlusive member distally through the distal opening to expel the occlusive member from the shaft and allow the occlusive member to expand to a first expanded state in which the occlusive member has a first shape and the one or more preferential bending regions are positioned between the proximal and distal end portions of the occlusive member, and
   wherein, when the occlusive member is in the first expanded state in the aneurysm cavity and coupled to the elongate member, proximal movement of the elongate member collapses a distal wall of the occlusive member proximally towards a proximal wall of the occlusive member, thereby transforming the occlusive member into a second expanded state in which the occlusive member has a second shape different than the first shape and the one or more preferential bending regions are closer to the aneurysm dome than both of the proximal and distal end portions.

2. The system of claim 1, further comprising an embolic element configured to be delivered to the aneurysm cavity through the elongate member while the elongate member is coupled to the distal end portion of the occlusive member.

3. The system of claim 2, wherein the embolic element is a liquid embolic, one or more embolic coils, or both.

4. The system of claim 1, wherein a portion of the occlusive member surrounding the elongate member at the opening is configured to slide relative to the elongate member as the occlusive member self-expands.

5. The system of claim 1, wherein all or a portion of the one or more preferential bending regions comprise a radiopaque material.

6. The system of claim 1, wherein the first expanded state is a globular shape and the second expanded state is a bowl shape.

7. The system of claim 1, wherein the distal wall conforms to the proximal wall when the occlusive member is in the second expanded state.

8. The system of claim 1, wherein the occlusive member comprises a plurality of braided filaments.

9. The system of claim 1, wherein the proximal end portion of the occlusive member does not include a connector.

10. The system of claim 1, wherein, in the second expanded state the occlusive member comprises at least two mesh layers, and wherein the occlusive member is configured to be positioned in the aneurysm such that the at least two mesh layers are positioned at a neck of the aneurysm.

11. A system comprising:
    an elongate shaft defining a lumen;
    an elongate member slidably disposed within the lumen of the elongate shaft, the elongate member having a proximal end region and a distal end region, wherein the distal end region is configured to be intravascularly positioned at or within an aneurysm cavity; and
    an occlusive member constrained within the lumen of the shaft, the occlusive member including a proximal end portion having an opening and a distal end portion detachably coupled to the distal end region of the elongate member, wherein the elongate member extends through the opening, and wherein, when the occlusive member is constrained within the lumen of the elongate shaft, the distal end portion is distal of the proximal end portion,
    wherein pushing the elongate member from a distal opening in the elongate shaft pulls the occlusive member distally through the distal opening to expel the occlusive member from the elongate shaft and allow the occlusive member to expand to a firsts expanded state in which the occlusive member has a globular shape including a first wall portion proximate a dome of the aneurysm and a second wall portion proximate a neck of the aneurysm, and
    wherein, when the occlusive member is in the first expanded state in the aneurysm cavity and coupled to the elongate member, proximal movement of the elongate member collapses the first wall portion towards the second wall portion, thereby transforming the occlusive member into a second expanded state in which the occlusive member has a bowl shape.

12. The system of claim 11, further comprising an embolic element configured to be delivered to the aneurysm cavity through the elongate member while the elongate member is coupled to the distal end portion of the occlusive member.

13. The system of claim 12, wherein the embolic element is a liquid embolic, one or more embolic coils, or both.

14. The system of claim 11, wherein a portion of the occlusive member surrounding the elongate member at the opening is configured to slide relative to the elongate member as the occlusive member self-expands.

15. The system of claim 11, wherein the occlusive member comprises one or more preferential bending regions about all or a portion of the circumference of the occlusive member.

16. The system of claim 15, wherein all or a portion of the one or more preferential bending regions comprise a radiopaque material.

17. The system of claim 11, wherein the occlusive member comprises a plurality of braided filaments.

18. The system of claim 11, wherein the proximal end portion of the occlusive member does not include a connector.

\* \* \* \* \*

UNITED STATES PATENT AND TRADEMARK OFFICE
CERTIFICATE OF CORRECTION

| | | |
|---|---|---|
| PATENT NO. | : 11,633,818 B2 | Page 1 of 1 |
| APPLICATION NO. | : 16/949568 | |
| DATED | : April 25, 2023 | |
| INVENTOR(S) | : Rhee et al. | |

It is certified that error appears in the above-identified patent and that said Letters Patent is hereby corrected as shown below:

In the Claims

In Column 34, in Claim 11, Line 61, delete "firsts" and insert -- first --, therefor.

Signed and Sealed this
Twenty-seventh Day of June, 2023

Katherine Kelly Vidal
*Director of the United States Patent and Trademark Office*